US010524908B2

(12) United States Patent
Peterson et al.

(10) Patent No.: US 10,524,908 B2
(45) Date of Patent: *Jan. 7, 2020

(54) CONTROLLED TIP RELEASE STENT GRAFT DELIVERY SYSTEM AND METHOD

(71) Applicant: Medtronic Vascular, Inc., Santa Rosa, CA (US)

(72) Inventors: Susan Rea Peterson, Santa Rosa, CA (US); Brian Glynn, Santa Rosa, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 144 days.

This patent is subject to a terminal disclaimer.

(21) Appl. No.: 15/689,063

(22) Filed: Aug. 29, 2017

(65) Prior Publication Data

US 2018/0008401 A1    Jan. 11, 2018

Related U.S. Application Data

(62) Division of application No. 14/284,508, filed on May 22, 2014, now Pat. No. 9,775,706, which is a division
(Continued)

(51) Int. Cl.
*A61F 2/06* (2013.01)
*A61F 2/24* (2006.01)
(Continued)

(52) U.S. Cl.
CPC ............... *A61F 2/243* (2013.01); *A61F 2/95* (2013.01); *A61F 2/966* (2013.01); *A61F 2/07* (2013.01); *A61F 2002/9665* (2013.01)

(58) Field of Classification Search
CPC ...... A61F 2/2427; A61F 2/243; A61F 2/2436; A61F 2/95; A61F 2/954; A61F 2/962;
(Continued)

(56) References Cited

U.S. PATENT DOCUMENTS 7,264,632 B2    9/2007   Wright et al.
2004/0082966 A1*  4/2004  WasDyke ................. A61F 2/01
                                                 606/200
(Continued)

FOREIGN PATENT DOCUMENTS

EP          1369098        12/2003
EP          1772120         4/2007
WO      WO2010/005524       1/2010

*Primary Examiner* — Melanie R Tyson
(74) *Attorney, Agent, or Firm* — Medler Ferro Woodhouse & Mills PLLC

(57) ABSTRACT

An apparatus and method of deploying a stent graft having a proximal anchor stent ring includes restraining proximal apexes of the proximal anchor stent ring between a spindle body of a spindle and a control release sleeve of a tapered tip. The control release sleeve is advanced relative to the spindle to release a first proximal apex through an opening in the control release sleeve while the remaining proximal apexes remain restrained by the control release sleeve. The control release sleeve is further advanced relative to the spindle to release the remaining proximal apexes from the control release sleeve. In another example, a stent capture fitting has variable length stent capture fitting arms. As the stent capture fitting is retracted, the proximal apexes of the proximal anchor stent ring are sequentially exposed from and released by the variable length stent capture fitting arms. By using the control release sleeve or the stent capture fitting, controlled sequential release of the proximal apexes is achieved.

20 Claims, 21 Drawing Sheets

Related U.S. Application Data of application No. 12/763,959, filed on Apr. 20, 2010, now Pat. No. 8,764,811.

(51) Int. Cl.
*A61F 2/966* (2013.01)
*A61F 2/95* (2013.01)
*A61F 2/07* (2013.01)

(58) Field of Classification Search
CPC .............. A61F 2/966; A61F 2002/9505; A61F 2002/9534; A61F 2002/9665
See application file for complete search history.

(56) References Cited

U.S. PATENT DOCUMENTS

| | | |
|---|---|---|
| 2005/0049667 A1* | 3/2005 | Arbefeuille ............... A61F 2/07 623/1.11 |
| 2006/0085057 A1 | 4/2006 | George |
| 2006/0276872 A1 | 12/2006 | Arbefeuille et al. |
| 2007/0135818 A1 | 6/2007 | Moore et al. |
| 2007/0163668 A1 | 7/2007 | Arbefeuille et al. |
| 2007/0208407 A1 | 9/2007 | Gerdts et al. |
| 2008/0114442 A1 | 5/2008 | Mitchell et al. |
| 2008/0114443 A1 | 5/2008 | Mitchell et al. |
| 2010/0268315 A1 | 10/2010 | Glynn et al. |

\* cited by examiner

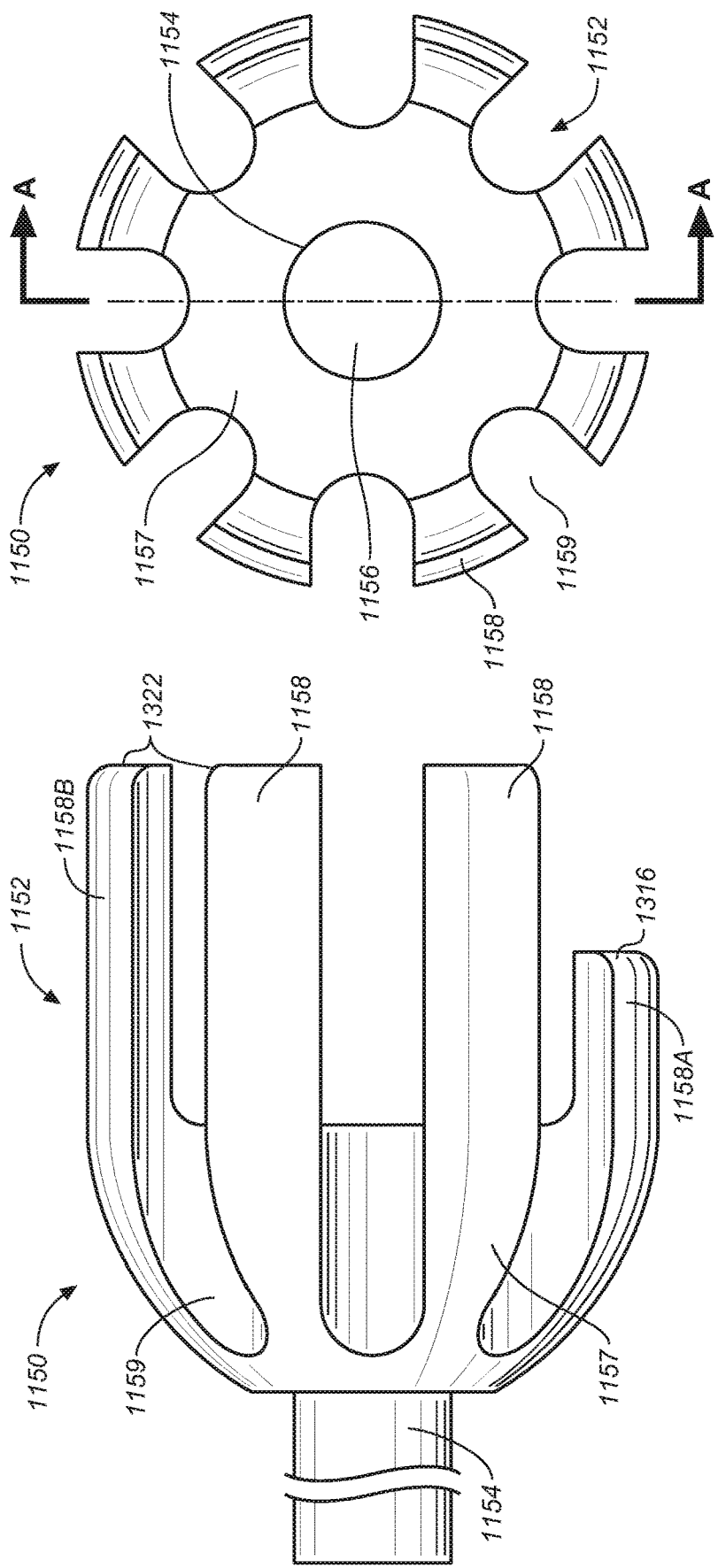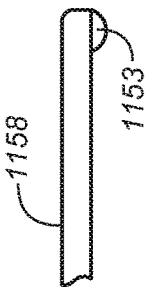
FIG. 14B
FIG. 14C
FIG. 14A

CONTROLLED TIP RELEASE STENT GRAFT DELIVERY SYSTEM AND METHOD

CROSS-REFERENCE TO RELATED APPLICATION

This application is a division of U.S. patent application Ser. No. 14/284,508, filed May 22, 2014, now allowed, which is a divisional of U.S. patent application Ser. No. 12/763,959 filed Apr. 20, 2010, now U.S. Pat. No. 8,764,811, which the disclosures of which are incorporated by reference herein in their entirety.

BACKGROUND OF THE INVENTION

Field of the Invention

This invention relates generally to medical devices and procedures, and more particularly to a method and system of deploying a stent graft in a vascular system.

Description of the Related Art

Prostheses for implantation in blood vessels or other similar organs of the living body are, in general, well known in the medical art. For example, prosthetic vascular grafts formed of biocompatible materials (e.g., Dacron or expanded, porous polytetrafluoroethylene (PTFE) tubing) have been employed to replace or bypass damaged or occluded natural blood vessels.

A graft material supported by a framework is known as a stent graft or endoluminal graft. In general, the use of stent grafts for treatment or isolation of vascular aneurysms and vessel walls which have been thinned or thickened by disease (endoluminal repair or exclusion) is well known.

Many stent grafts, are "self-expanding", i.e., inserted into the vascular system in a compressed or contracted state, and permitted to expand upon removal of a restraint. Self-expanding stent grafts typically employ a wire or tube configured (e.g., bent or cut) to provide an outward radial force and employ a suitable elastic material such as stainless steel or nitinol (nickel-titanium). Nitinol may additionally be conditioned to utilize shape memory properties of the alloy.

The self-expanding stent graft is typically configured in a tubular shape and sized for implantation to have a slightly greater diameter than the diameter of the blood vessel in which the stent graft is intended to be used. In general, rather than providing a repair using open surgery which is traumatic and highly invasive, stents and stent grafts are typically deployed through a less invasive intraluminal delivery, i.e., cutting through the skin to access a lumen or vasculature or percutaneously via successive dilatation, at a convenient (and less traumatic) entry point, and routing a catheter delivery system containing a stent graft through the lumen to the site where the stent graft is to be deployed.

Intraluminal deployment in one example is effected using a delivery catheter with coaxial inner tube, sometimes called the plunger, and outer tube, sometimes called the sheath, arranged for relative axial movement. The stent graft is compressed and disposed within the distal end of the sheath in front of the inner tube.

The catheter is then maneuvered, typically routed though a lumen (e.g., vessel), until the end of the catheter (and the stent graft) is positioned in the vicinity of the intended treatment site. The inner tube is then held stationary while the sheath of the delivery catheter is withdrawn. The inner tube contains a stent stop which prevents the stent graft from moving back as the sheath is withdrawn.

As the sheath is withdrawn, the stent graft is gradually exposed from a proximal end to a distal end of the stent graft, the exposed portion of the stent graft radially expands so that at least a portion of the expanded portion is in substantially conforming surface contact with a portion of the interior of the lumen, e.g., blood vessel wall.

The proximal end of the stent graft is the end closest to the heart by way of blood flow path whereas the distal end is the end furthest away from the heart by way of blood flow path during deployment. In contrast and of note, the distal end of the catheter is usually identified to the end that is farthest from the operator (handle) while the proximal end of the catheter is the end nearest the operator (handle). For purposes of clarity of discussion, as used herein, the distal end of the catheter is the end that is farthest from the operator (the end furthest from the handle) while the distal end of the stent graft is the end nearest the operator (the end nearest the handle), i.e., the distal end of the catheter and the proximal end of the stent graft are the ends furthest from the handle while the proximal end of the catheter and the distal end of the stent graft are the ends nearest the handle. However, those of skill in the art will understand that depending upon the access location, the stent graft and delivery system description may be consistent or opposite in actual usage.

SUMMARY OF THE INVENTION

A method of deploying a stent graft including a proximal anchor stent ring includes restraining proximal apexes of the proximal anchor stent ring between a spindle body of a spindle and a control release sleeve of a tapered tip. The control release sleeve is advanced relative to the spindle to release a first proximal apex through an opening in the control release sleeve while the remaining proximal apexes remain restrained by the control release sleeve. The control release sleeve is further advanced relative to the spindle to release the remaining proximal apexes from the control release sleeve. By using the control release sleeve, controlled sequential release of the proximal apexes is achieved.

In another example, a stent capture fitting has variable length stent capture fitting arms. As the stent capture fitting is retracted, the proximal apexes of the proximal anchor stent ring are sequentially exposed from and released by the variable length stent capture fitting arms.

These and other features according to the present invention will be more readily apparent from the detailed description set forth below taken in conjunction with the accompanying drawings.

BRIEF DESCRIPTION OF THE DRAWINGS

FIGS. 14A & 14B are a side and end view, respectively, of a portion of a stent capture assembly;

FIG. 14C is a side view of another embodiment of a stent capture fitting arm;

In the following description, the same or similar elements are labeled with the same or similar reference numbers.

DETAILED DESCRIPTION

Figure 5:
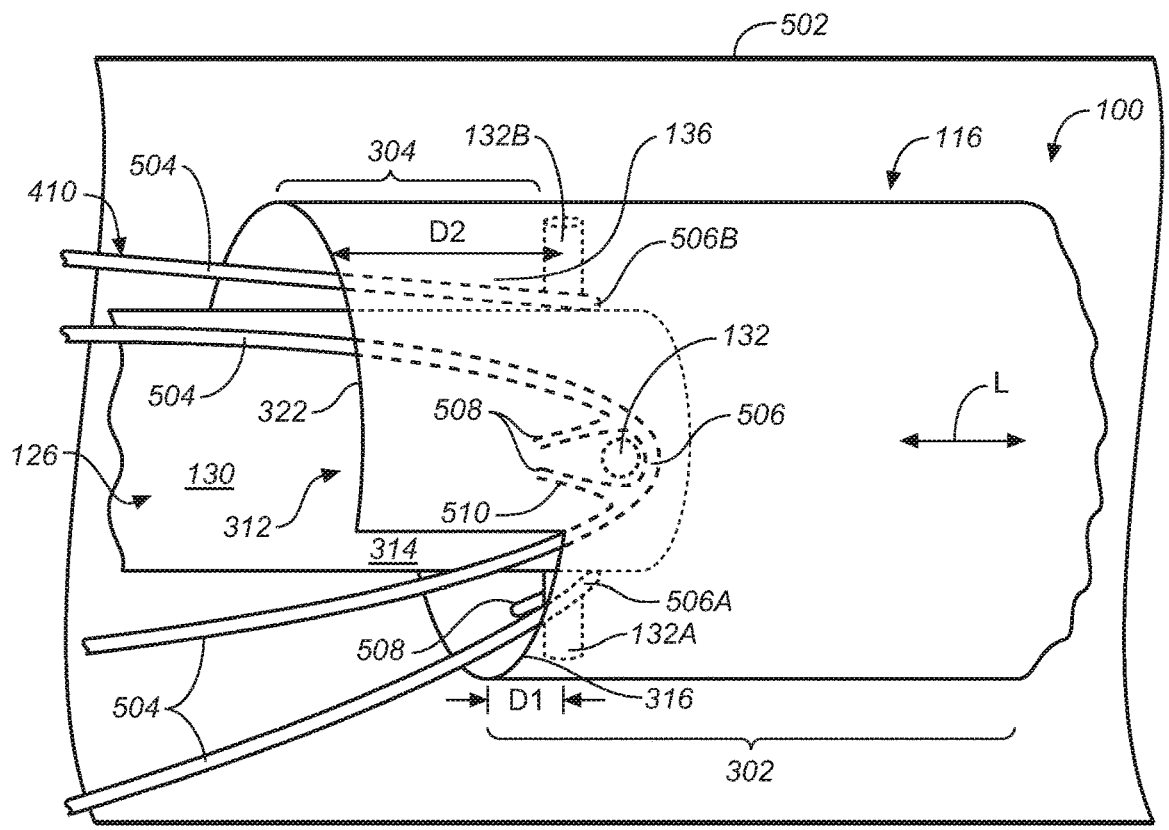
FIG. 5 is an enlarged oblique view of the stent graft delivery system of FIG. 4 in a vessel after retraction of the primary sheath.
Figure 6:
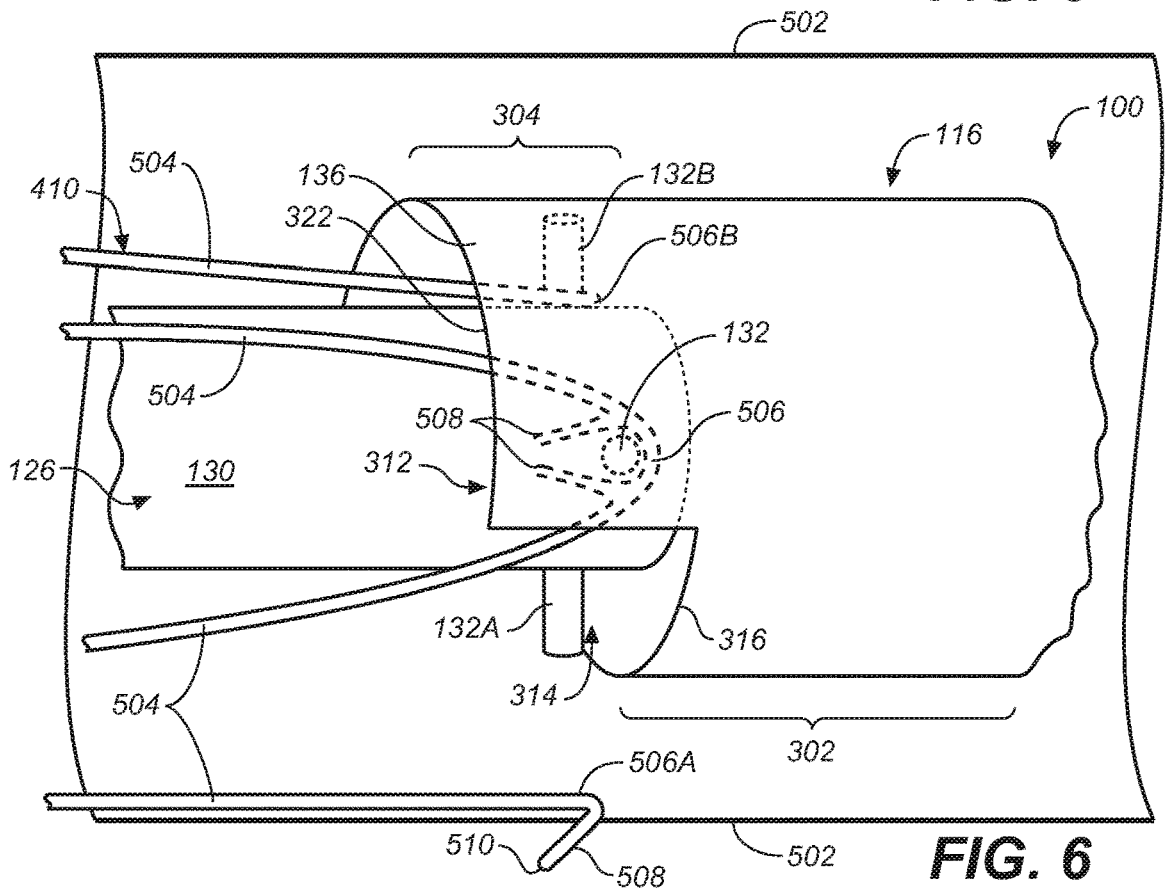
FIG. 6 is an oblique view of the stent graft delivery system of FIG. 5 after partial movement of the release sleeve having released one crown of a proximal anchor stent ring of the stent graft.
Figure 7:
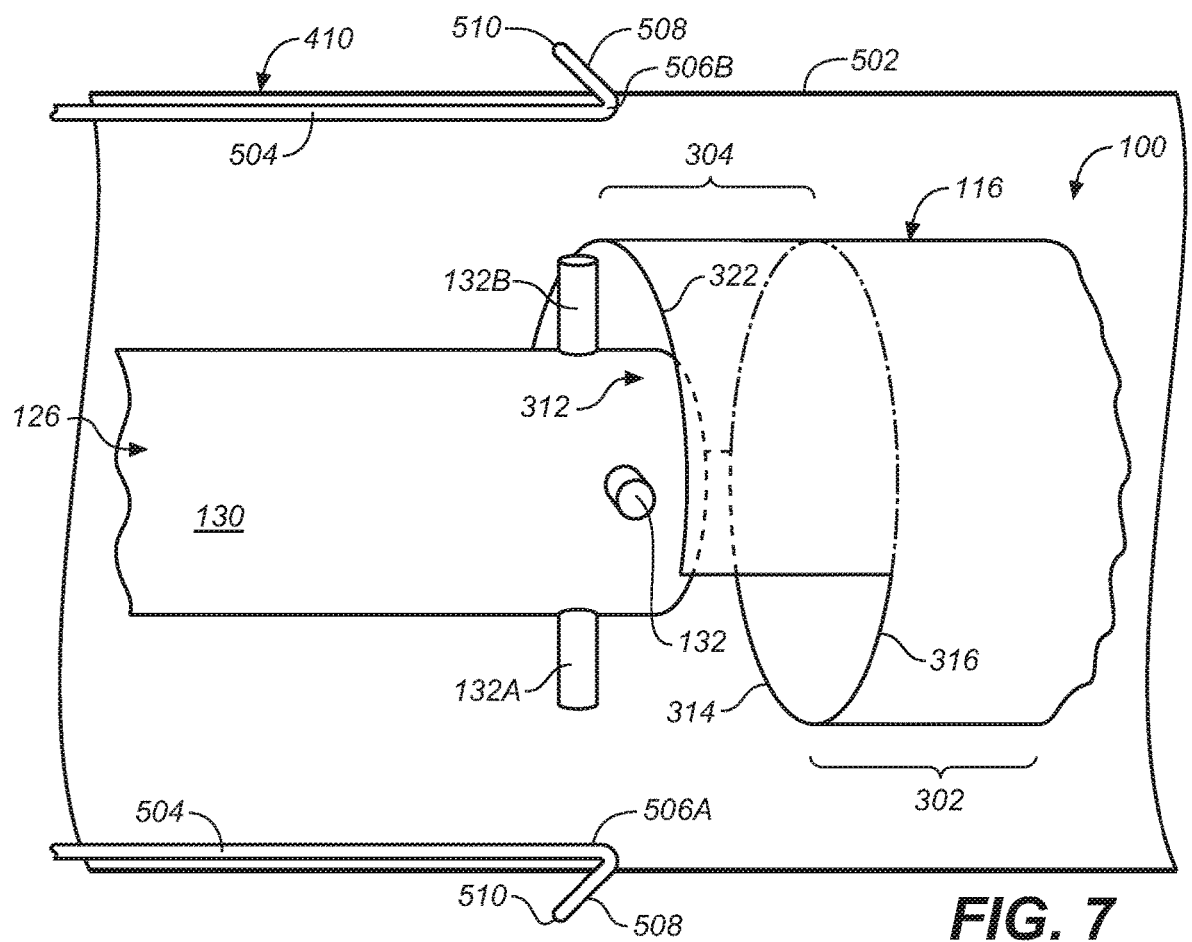
FIG. 7 is an oblique view of the stent graft delivery system of FIG. 6 after further movement of the release sleeve to achieve complete deployment of the proximal anchor stent ring of the stent graft.

As an overview, referring to FIG. 5, a method of deploying a stent graft having a proximal anchor stent ring 410 includes restraining proximal apexes, e.g., 506, including proximal apexes 506A, 506B of proximal anchor stent ring 410 between a spindle body 130 of a spindle 126 and a control release sleeve 116 of a tapered tip (which is only partially shown in FIG. 5). Referring now to FIGS. 5 and 6 together, control release sleeve 116 is advanced relative to spindle 126 to release proximal apex 506A by uncovering the apex from beneath the sleeve as the edge of opening 314 in control release sleeve 116 is advanced while the remaining proximal apexes 506 including proximal apex 506B remain covered, thereby being restrained by control release sleeve 116. Referring now to FIGS. 6 and 7 together, control release sleeve 116 is shown further advanced relative to spindle 126 to release the remaining proximal apexes, e.g., 506 including proximal apex 506B from control release sleeve 116. By using control release sleeve 116, controlled sequential release of proximal apexes, e.g., 506, is achieved.

Figure 1:
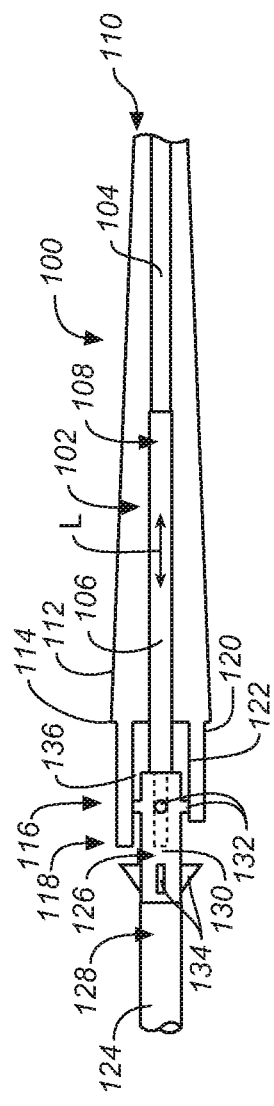
FIG. 1 is a schematic cross-sectional view of a stent graft delivery system without a stent graft and primary sheath.

Now in more detail, FIG. 1 is a schematic cross-sectional view of a stent graft delivery system 100 without a stent graft and primary sheath in accordance with one embodiment. Stent graft delivery system 100 includes a tapered tip 102 that provides trackability in tight and tortuous vessels. Tapered tip 102 includes a guidewire lumen 104 therein for connecting to adjacent members and allowing passage of a guidewire through tapered tip 102. Other tip shapes such as bullet-shaped tips could also be used.

An inner tube 106 defines a lumen, e.g., a guidewire lumen, therein. A distal end 108 of inner tube 106 is located within and secured to tapered tip 102, i.e., tapered tip 102 is mounted on inner tube 106. As shown in FIG. 1, the lumen of inner tube 106 is in fluid communication with guidewire lumen 104 of tapered tip 102 such that a guidewire can be passed through inner tube 106 and out distal end 108, through guidewire lumen 104 of tapered tip 102, and out a distal end 110 of tapered tip 102.

Tapered tip 102 includes a tapered outer surface 112 that gradually increases in diameter. More particularly, tapered outer surface 112 has a minimum diameter at distal end 110 and gradually increases in diameter proximally, i.e., in the direction of the operator (or handle of stent graft delivery system 100), from distal end, e.g., 110.

Tapered outer surface 112 extends proximally to a primary sheath abutment surface (shoulder) 114 of tapered tip 102. Primary sheath abutment surface 114 is an annular ring perpendicular to a longitudinal axis "L" of stent graft delivery system 100 and tapered tip 102.

Tapered tip 102 further includes a control release sleeve 116 extending proximally from primary sheath abutment surface 114. Generally, control release sleeve 116 is at a proximal end 118 of tapered tip 102. Control release sleeve 116 extends proximally and longitudinally from primary sheath abutment surface 114. Control release sleeve 116 includes an outer partially cutaway cylindrical surface 120 and an inner partially cutaway cylindrical surface 122.

Stent graft delivery system 100 further includes a middle member 124 having a spindle 126 located at and fixed to a distal end 128 of middle member 124. Spindle 126 includes a spindle body 130 having a cylindrical outer surface, a plurality of spindle pins, e.g., 132, protruding radially outward from spindle body 130, and a plurality of primary sheath guides, e.g., 134, protruding radially outward from spindle body 130. Primary sheath guides 134 guide the primary sheath into position over control release sleeve 116 (see FIG. 4, for example).

Figure 2:
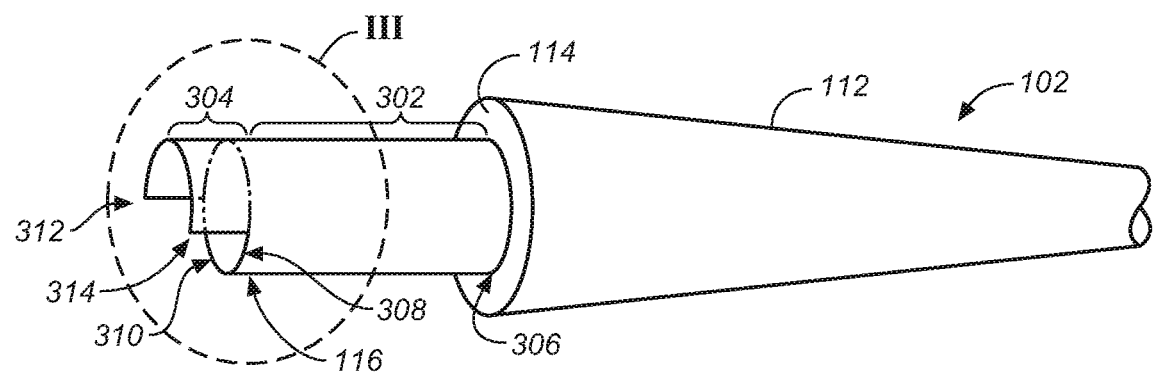
FIG. 2 is an oblique view of a tapered tip of the stent graft delivery system of FIG. 1.
Figure 3:
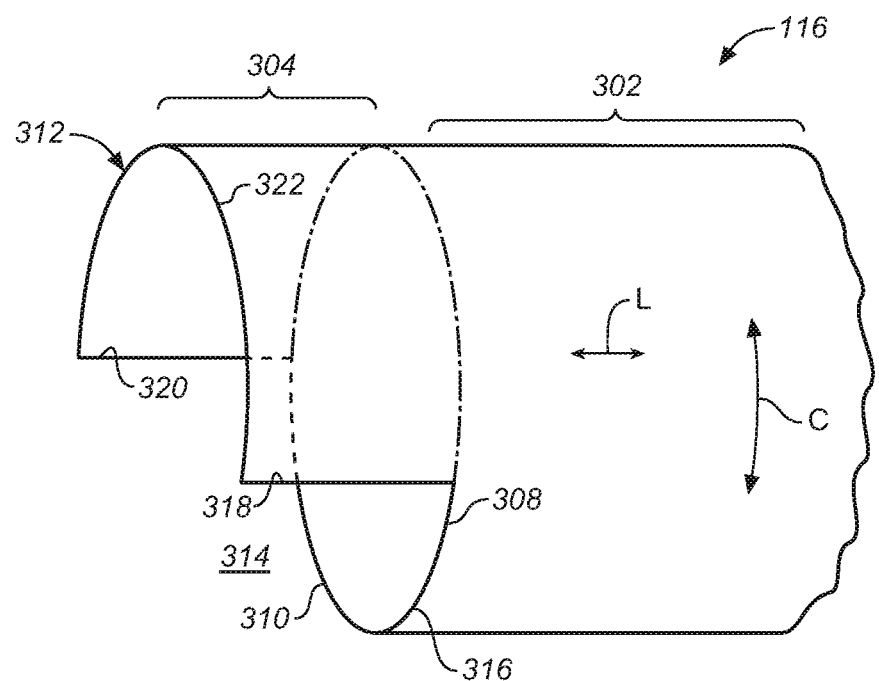
FIG. 3 is an enlarged oblique view of the region III of a control release sleeve of the tapered tip of FIG. 2.

FIG. 2 is an oblique view of tapered tip 102 of stent graft delivery system 100 of FIG. 1 in accordance with one example (embodiment). FIG. 3 is an enlarged oblique view of the region III of control release sleeve 116 of tapered tip 102 of FIG. 2.

Referring now to FIGS. 1, 2, and 3 together, control release sleeve 116 includes a cylindrical wall portion 302 and a control release portion 304. Cylindrical wall portion 302 is cylindrical and extends proximally from primary sheath abutment surface 114. More particularly, a distal end 306 of cylindrical wall portion 302 connects to primary sheath abutment surface 114. Cylindrical wall portion 302 extends proximally from distal end 306 to a proximal end 308 of cylindrical wall portion 302.

Control release portion 304 is connected to and extends proximally from proximal end 308 of cylindrical wall portion 302. More particularly, a distal end 310 of control release portion 304 connects to proximal end 308 of cylindrical wall portion 302. Control release portion 304 extends proximally from distal end 310 to a proximal end 312 of control release portion 304.

In one example, cylindrical wall portion 302 and control release portion 304 are integral, i.e., are a single piece and not a plurality of separate pieces connected together. For example, control release sleeve 116 is formed by using a special pattern to cut an already existing hypotube.

Control release portion 304 is generally cylindrical but includes an opening 314, sometimes called a space or window at a portion of the edge of control release sleeve 116. Stated another way, control release portion 304 is a hollow cylinder (tube), except has a portion of the end of cylinder cutaway creating a non uniform proximal length edge beyond which can be referred to as forming opening 314. Accordingly, opening 314 is sometimes called a cutaway portion of the cylinder of control release portion 304 and control release portion 304 is sometimes called a partially cutaway cylinder. Illustratively, control release sleeve 116 as shown in FIG. 3 is also sometimes described as having a single step.

Opening 314 is defined by a circumferential edge 316 of control release sleeve 116, a first longitudinal edge 318 of control release sleeve 116, and a second longitudinal edge 320 of control release sleeve 116. Circumferential edge 316 traces a partial square or ninety degree cut that extends along the circumference C of control release sleeve 116 between longitudinal edges 318, 320. Circumferential edge 316 is at proximal end 308 of cylindrical wall portion 302 and distal end 310 of control release portion 304. Longitudinal edges 318, 320 are parallel to longitudinal axis "L" of control release sleeve 116 and extend between proximal end 312 of control release portion 304 and circumferential edge 316.

Control release portion 304 is defined by a circumferential edge 322 of control release sleeve 116 and longitudinal edges 318, 320 of control release sleeve 116. Circumferential edge 322 traces a partial square or ninety degree cut that extends along the circumference C of control release sleeve 116 between longitudinal edges 318, 320. Circumferential edge 322 is at proximal end 312 of control release portion 304. Longitudinal edges 318, 320 extend between circumferential edge 316, sometimes called a first circumferential edge, and circumferential edge 322, sometimes called a second circumferential edge. The distance between the first circumferential edge 316 and the second circumferential edge 322 is at least one to two millimeters and can be greater.

As illustrated in FIG. 1, spindle 126 is configured to slip inside of control release sleeve 116 such that spindle pins 132 are directly adjacent to, or in contact with, inner partially cutaway cylindrical surface 122 of control release sleeve 116. Spindle pins 132 extend from spindle body 130 towards and to control release sleeve 116.

Generally, the diameter to which spindle pins 132 extend from spindle body 130 is approximately equal to, or slightly less than, the diameter of inner partially cutaway cylindrical surface 122 of control release sleeve 116 allowing spindle pins 132 to snugly fit inside of control release sleeve 116. A space (or gap) 136 exists between inner partially cutaway cylindrical surface 122 and spindle body 130.

Inner tube 106 is within and extends through middle member 124 and spindle 126. Inner tube 106 and thus tapered tip 102 is moved along longitudinal axis "L" (longitudinally moved) relative to middle member 124 and thus spindle 126 to release the proximal end of a stent graft as discussed further below. The term "stent graft" used herein should be understood to include stent grafts and other forms of endoprosthesis.

Figure 4:
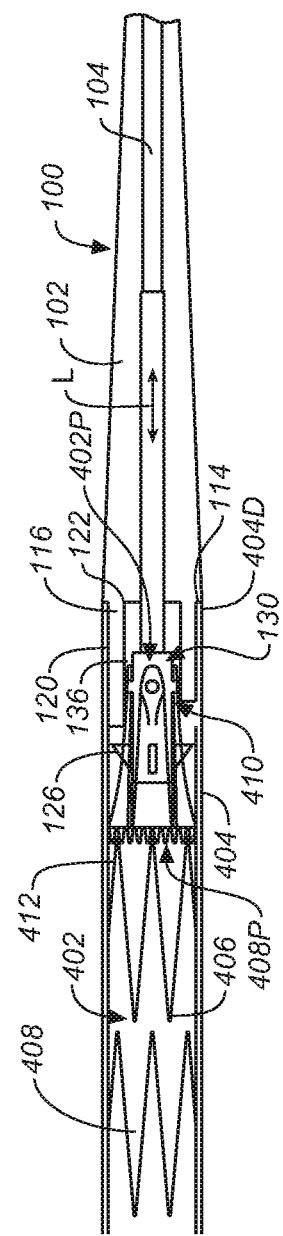
FIG. 4 is a schematic cross-sectional view of the stent graft delivery system of FIG. 1 including a stent graft located within a retractable primary sheath before deployment.

FIG. 4 is a schematic cross-sectional view of stent graft delivery system 100 of FIG. 1 including a stent graft 402 located within a retractable primary sheath 404 in a pre-deployed compressed configuration.

Primary sheath 404 is a hollow tube and defines a lumen 406 therein through which middle member 124 and inner tube 106 extend. Primary sheath 404 is in a pre-deployment compressed configuration in FIG. 4. Primary sheath 404 is moved proximally along longitudinal axis "L", sometimes called retracted, relative to middle member 124/spindle 126 and thus stent graft 402 (whose proximal end is held captured by the outer tube and spindle) to deploy a portion of stent graft 402 as discussed further below.

In one example, stent graft 402 is a self-expanding stent graft such that stent graft 402 self-expands upon being released from its radially constrained position. In accordance with this example, stent graft 402 includes a graft material 408, e.g., formed of ePTFE, polyester or Dacron material, and a plurality of resilient self-expanding support structures, e.g., formed of super elastic self-expanding memory material such as nitinol. Graft material 408 includes a proximal end 408P.

The support structures include a proximal anchor stent ring 410 at a proximal end 402P of stent graft 402 and one or more stent rings 412 distal to proximal anchor stent ring 410. Proximal anchor stent ring 410 is attached to proximal end 408P of graft material 408. Proximal anchor stent ring 410 and stent rings 412 are attached to graft material 408, e.g., by sutures, adhesive, or other means.

As shown in FIG. 4, stent graft 402 is in a radially constrained configuration over (or surrounding) middle member 124 and spindle 126. Stent graft 402 is located within and held radially compressed by primary sheath 404. Further, proximal apexes, sometimes called crowns or the tip, of proximal anchor stent ring 410 of stent graft 402 are radially constrained and held in position in space 136 between spindle body 130 and control release sleeve 116.

Generally, graft material 408 of stent graft 402 is held radially constrained by primary sheath 404 and the proximal apexes of proximal anchor stent ring 410 are held radially constrained by control release sleeve 116 allowing sequential and independent deployment of graft material 408 and proximal apexes of proximal anchor stent ring 410 of stent graft 402.

Primary sheath 404 includes a distal end 404D adjacent to or in abutting contact with primary sheath abutment surface 114 of tapered tip 102. Distal end 404D fits snugly around control release sleeve 116 and in one example lightly presses radially inward on outer partially cutaway cylindrical surface 120 of control release sleeve 116.

FIG. 5 is an enlarged oblique view of stent graft delivery system 100 of FIG. 4 in a vessel 502 after retraction of primary sheath 404. Referring now to FIGS. 4 and 5 together, stent graft delivery system 100 is positioned within vessel 502 as those of skill in the art will understand in light of this disclosure.

Once positioned within vessel 502, primary sheath 404 is partially or completely retracted such that distal end 404D is spaced apart from tapered tip 102. Further, due to the retraction of primary sheath 404, a portion of stent graft 402 is exposed and partially deployed. However, the proximal portion of proximal anchor stent ring 410 is restrained by control release sleeve 116 and thus remains constrained.

More particularly, proximal anchor stent ring 410 includes a zigzag pattern of struts 504 alternating between proximal apexes 506 and the distal apexes of proximal anchor stent ring 410. The distal apexes are attached to graft material 408 of stent graft 402 as illustrated in FIG. 4.

Proximal anchor stent ring 410 further may include anchor pins 508 (as represented by dashed lines). More particularly, a pair of anchor pins 508 is located on struts 504 adjacent each proximal apex 506. In accordance with this example, anchor pins 508 include distal tips 510, e.g., sharp points, which facilitate penetration of anchor pins 508 into vessel 502 in which stent graft 402 is being deployed.

As illustrated, proximal apexes 506 of proximal anchor stent ring 410 are held radially constrained by control release sleeve 116. More particularly, each proximal apex 506 extends around a spindle pin 132 and is located and secured within space 136 between spindle body 130 and control release sleeve 116. Specifically, each proximal apex 506 is located and secured within space 136 between spindle body 130 and cylindrical wall portion 302 of control release sleeve 116.

To illustrate, a first proximal apex 506A of the plurality of proximal apexes, e.g., 506, extends around (over) a first spindle pin 132A of the plurality of spindle pins 132 and is located and secured (constrained to remain) within space 136 between spindle body 130 and control release sleeve 116. Similarly, a second proximal apex 506B of the plurality of proximal apexes 506 extends around a second spindle pin 132B of the plurality of spindle pins 132 and is located and secured within space 136 between spindle body 130 and control release sleeve 116. Although three proximal apexes 506 are illustrated in FIG. 5 corresponding to a proximal anchor stent ring having a total of four proximal apexes, in other examples, a similar proximal anchor stent ring has more or less than four proximal apexes.

Further, anchor pins, e.g., 508, extend radially from spindle body 130 and occupy a portion of the space 136 between spindle body 130 and control release sleeve 116 to somewhat act as spacers therebetween.

FIG. 6 is an oblique view of stent graft delivery system 100 of FIG. 5 after deployment of some crowns of proximal anchor stent ring 410 of stent graft 402. The stepped or variable pitch sleeve on the delivery system, has the benefit that that it allows adjustable deployment of the proximal edge of the stent graft. This is useful in situations where renal arteries are at different heights (e.g. deploy the anchor pins on the high side first, then move the delivery system distally before deploying the anchor pins on the opposite side to match the lower target) and can enable (be workable) when only short seal zones are available. Other situations in which adjustable deployment could be helpful would include avoiding partially calcified regions or areas where thrombosis has formed that could affect acute seal and long-term migration. Referring now to FIGS. 5 and 6 together, tapered tip 102 is advanced relative to spindle 126 to expose and release proximal apex 506A of proximal anchor stent ring 410.

More particularly, as illustrated in FIG. 5, prior to advancement of tapered tip 102 relative to spindle pins, e.g., 132, a first distance D1 between spindle pin 132A and circumferential edge 316 and thus opening 314 in a direction parallel to longitudinal axis "L" is less than a second distance D2 (by at least 1-2 mm.) between the remaining spindle pins, e.g., 132, including spindle pin 132B and circumferential edge 322 and thus proximal end 312. Accordingly, as tapered tip 102 is advanced, circumferential edge 316 is advanced past spindle pin 132A before circumferential edge 322 is advanced past the remaining spindle pins 132 including spindle pin 132B. As circumferential edge 316 is advanced past spindle pin 132A, proximal apex 506A is exposed and released through opening 314 as illustrated in FIG. 6. However, due to the greater initial distance D2 between the remaining spindle pins 132 and circumferential edge 322, circumferential edge 322 is not advanced past the remaining spindle pins 132 and respective proximal apexes 506, but remains proximal thereto as also illustrated in FIG. 6.

Upon being released from control release sleeve 116, proximal apex 506A (and generally the associated portion of proximal anchor stent ring 410) self-expands into vessel 502 in which stent graft 402 is being deployed.

Anchor pins 508 associated with proximal apex 506A penetrate into vessel 502 thus anchoring proximal apex 506A and thus a portion of proximal anchor stent ring 410 to vessel 502.

In accordance with this example, the remaining proximal apexes 506, i.e., the proximal apexes 506 including proximal apex 506B other than proximal apex 506A, remain radially constrained by control release sleeve 116. More particularly, the remaining proximal apexes 506 extend around spindle pins 132 and are located and secured within space 136 between spindle body 130 and control release sleeve 116. Specifically, the remaining proximal apexes 506 are located and secured within space 136 between spindle body 130 and control release portion 304 of control release sleeve 116.

To illustrate, proximal apex 506B remains extended around spindle pin 132B and located and secured within space 136 between spindle body 130 and control release sleeve 116, i.e., control release portion 304 of control release sleeve 316.

By using control release sleeve 116, controlled release of proximal apex 506A while restraint of the remaining proximal apexes 506 is achieved. Although the controlled release of a single proximal apex 506A is illustrated and discussed, in light of this disclosure, those of skill in the art will understand that in other examples a first set of proximal apexes are released while a second set of proximal apexes are restrained, i.e., the proximal apexes are released in two stages.

FIG. 7 is an oblique view of stent graft delivery system 100 of FIG. 6 after complete deployment of proximal anchor stent ring 410 of stent graft 402. Referring now to FIGS. 6 and 7 together, tapered tip 102 is advanced relative to spindle 126 to expose and release the remaining proximal apexes 506 of proximal anchor stent ring 410 thus completely deploying proximal anchor stent ring 410. More particularly, as circumferential edge 322 is advanced past the remaining spindle pins 132, the remaining proximal apexes 506 are exposed and released.

Upon being released from control release sleeve 116, the remaining proximal apexes 506 (and generally the associated portion of proximal anchor stent ring 410) self-expand into vessel 502 in which stent graft 402 is being deployed.

The remaining anchor pins 508 associated with the remaining proximal apexes 506 extend and penetrate into vessel 502 thus anchoring the remaining proximal apexes 506 and thus the remaining portion of proximal anchor stent ring 410 to vessel wall 504.

In one example, proximal apex 506A is deployed at the highest desired location within a short necked abdominal aorta with renal arteries at significantly different heights. After proximal apex 506A is deployed, stent graft delivery system 100 is pulled down as needed. Control release sleeve 116 is further advanced to release the remaining proximal apexes 506 and thus engage the remaining anchor pins 508 within the lower regions within the short necked abdominal aorta.

Referring again to FIG. 4, in one example, primary sheath 404 is only partially retracted prior to deployment of proximal anchor set ring 410. In accordance with this example, after deployment and anchoring of proximal anchor stent ring 410 to vessel 502 as discussed above, primary sheath 404 is fully retracted to fully deploy stent graft 402.

However, in another example, primary sheath 404 is fully retracted prior to release of proximal anchor stent ring 410. More particularly, primary sheath 404 is fully retracted while proximal apexes 506 of proximal anchor stent ring 410 are still radially constrained by control release sleeve 116.

Figure 8:
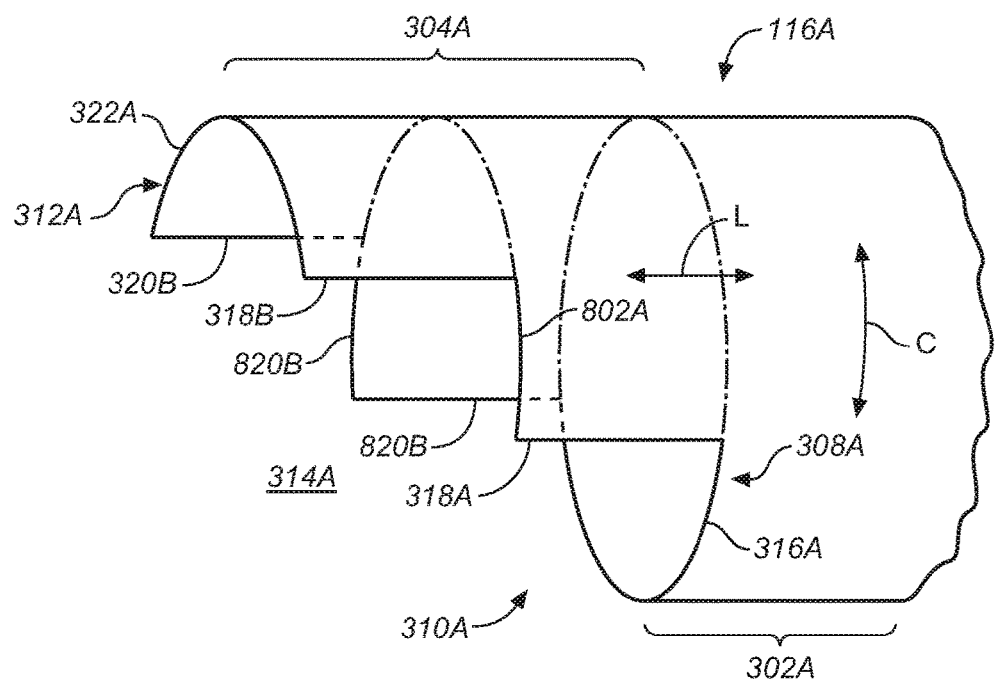
FIGS. 8, 9, 10 are oblique views of the proximal edges of various other control release sleeves that might be used.

FIG. 8 is an oblique view of a control release sleeve 116A in accordance with another example (embodiment). Referring now to FIG. 8, control release sleeve 116A is formed with a plurality of steps.

Control release sleeve 116A includes a cylindrical wall portion 302A and a control release portion 304A. Cylindrical wall portion 302A is similar to cylindrical wall portion 302 of control release sleeve 116 as discussed above and so is not repeated here.

Control release portion 304A is connected to and extends proximally from a proximal end 308A of cylindrical wall portion 302A. More particularly, a distal end 310A of control release portion 304A is connected to proximal end 308A of cylindrical wall portion 302A. Control release portion 304A extends proximally from distal end 310A to a proximal end 312A of control release portion 304A.

Control release portion 304A is generally cylindrical but includes a variable size opening 314A, sometimes called a variable size space, within control release sleeve 116A. Stated another way, control release portion 304A is a hollow cylinder, except has a portion of the cylinder cutaway thus forming variable size opening 314A. Accordingly, variable size opening 314A is sometimes called a cutaway portion of the cylinder of control release portion 304A and control release portion 304A is sometimes called a partially cutaway cylinder.

Variable size opening 314A is defined by a first circumferential edge 316A, a first longitudinal edge 318A, a second longitudinal edge 320A, a second circumferential edge 802A, a third circumferential edge 802B, a third longitudinal edge 318B, and a fourth longitudinal edge 320B.

Circumferential edge 316A is perpendicular, though in practice it may be slight angled or inclined toward sleeve 116A and extends along the circumference C of control release sleeve 116A between longitudinal edges 318A, 320A. Circumferential edge 316A is at proximal end 308A of cylindrical wall portion 302A and distal end 310A of control release portion 304A.

Longitudinal edge 318A is parallel to longitudinal axis "L" of control release sleeve 116A and extends between circumferential edge 316A and circumferential edge 802A. Longitudinal edge 320A is parallel to longitudinal axis "L" of control release sleeve 116A and extends between circumferential edge 316A and circumferential edge 802B.

Circumferential edge 802A extends along the circumference C of control release sleeve 116A between longitudinal edges 318A, 318B. Circumferential edge 802B extends along the circumference C of control release sleeve 116A between longitudinal edges 320A, 320B. Circumferential edges 802A, 802B are located along longitudinal axis "L" between distal end 310A and proximal end 312A of control release portion 304A.

Longitudinal edge 318B is parallel to longitudinal axis "L" of control release sleeve 116A and extends between circumferential edge 802A and proximal end 312A of control release portion 304A. Longitudinal edge 320B is parallel to longitudinal axis "L" of control release portion 304A and extends between circumferential edge 802B and proximal end 312A of control release portion 304A.

Accordingly, variable size opening 314A is larger at proximal end 312A between longitudinal edges 318B, 320B than at distal end 310A between longitudinal edges 318A, 320A and so is called a variable size opening.

Control release portion 304A is defined by a fourth circumferential edge 322A of control release sleeve 116A, circumferential edges 802A, 802B, longitudinal edges 318A, 318B, 320A, 320B of control release sleeve 116. Circumferential edge 322A extends along the circumference C of control release sleeve 116A between longitudinal edges 318B, 320B. Circumferential edge 322A is at proximal end 312A of control release portion 304A. Longitudinal edges 318B, 320B extend between circumferential edge 322A and circumferential edges 802A, 802B of control release portion 304, respectively.

In a manner similar to that discussed above in reference to FIGS. 5, 6, 7, as control release sleeve 116A is advanced, circumferential edge 316A is advanced beyond a first set (one or more) of spindle pins 132 thus releasing the respective first set of proximal apexes 506. As control release sleeve 116A is further advanced, circumferential edges 802A, 802B are advanced beyond a second set (one or more) of spindle pins 132 thus releasing the respective second set of proximal apexes 506. Finally, as control release sleeve 116A is further advanced, circumferential edge 322A is advanced beyond a third set (one or more) of spindle pins 132 thus releasing the respective third set of proximal apexes 506. In this manner, three sequential controlled releases of proximal apexes 506 is achieved, i.e., proximal apexes 506 are released in three stages.

Although a single step control release sleeve 116 is illustrated and discussed above in reference to FIGS. 1-7 and a two step control release sleeve 116A is discussed above in reference to FIG. 8, in other examples, similar control release sleeve are formed with more than two steps or steps having other configurations to achieve sequential controlled releases of the proximal apexes.

Figure 9:
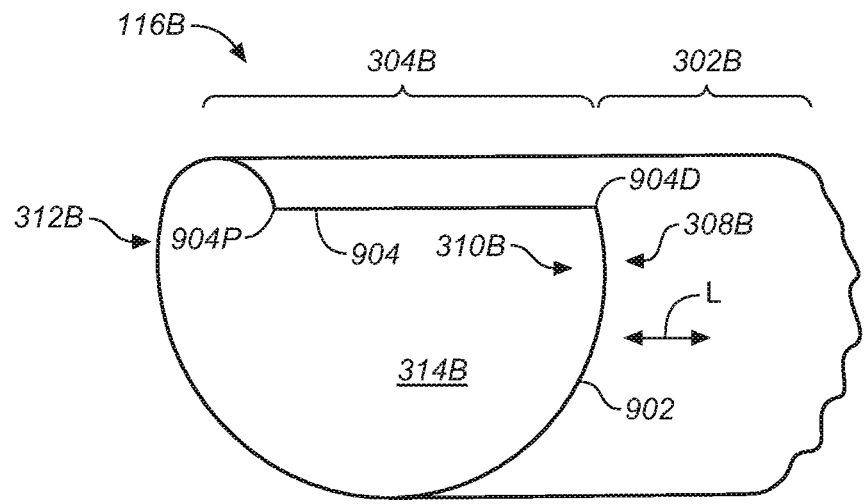

FIG. 9 is an oblique view of a control release sleeve 116B in accordance with yet another example. Referring now to FIG. 9, control release sleeve 116B includes a cylindrical wall portion 302B and a control release portion 304B. Cylindrical wall portion 302B is similar to cylindrical wall portion 302 of control release sleeve 116 as discussed above and so is not repeated here.

Control release portion 304B is connected to and extends proximally from a proximal end 308B of cylindrical wall portion 302B. More particularly, a distal end 310B of control release portion 304B is connected to proximal end 308B of cylindrical wall portion 302B. Control release portion 304B extends proximally from distal end 310B to a proximal end 312B of control release portion 304B.

Control release portion 304B is generally cylindrical but includes a variable size opening 314B, sometimes called a variable size space, within control release sleeve 116B. Stated another way, control release portion 304B is a hollow cylinder, except has a portion of the cylinder cutaway thus forming variable size opening 314B. Accordingly, variable size opening 314B is sometimes called a cutaway portion of the cylinder of control release portion 304B and control release portion 304B is sometimes called a partially cutaway cylinder.

Variable size opening 314B is defined by a left hand helical edge 902 and a longitudinal edge 904. Longitudinal edge 904 is parallel to longitudinal axis "L" of control release sleeve 116B. Longitudinal edge 904 has a proximal end 904P at proximal end 312B of control release portion 304B and a distal end 904D at distal end 310B of control release portion 304B.

Left hand helical edge 902 extends between proximal end 904P and distal end 904D of longitudinal edge 904. Left hand helical edge 902 is the form of a left hand helix. Although the terms "helical" and "helix" are used herein, it is to be understood that the described features may not be exactly helical and a helix but only approximately helical and a helix and may include variation therein.

Variable size opening 314B is larger at proximal end 312B than at distal end 310B between longitudinal edge 904 and left hand helical edge 902 and so is called a variable size opening.

Control release portion 304B is defined by left hand helical edge 902 and longitudinal edge 904.

In a manner similar to that discussed above in reference to FIGS. 5, 6, 7, as control release sleeve 116B is advanced, left hand helical edge 902 is sequentially advanced beyond spindle pins 132 thus releasing the respective proximal apexes 506 until all proximal apexes 506 have been released. More particularly, proximal apexes 506 are released radially sequentially clockwise when viewed in the distal direction (when viewed from the handle), i.e., one at a time in a clockwise circumferential direction. In this manner, sequential controlled release of proximal apexes 506 is achieved. In one example, the pitch of left hand helical edge 902 is varied to obtain a desired release timing of proximal apexes 506. While a helix is shown, a progressive edge pattern that is not perfect or approximately a helix may also be used, as will be understood by persons skilled in the art.

Figure 10:
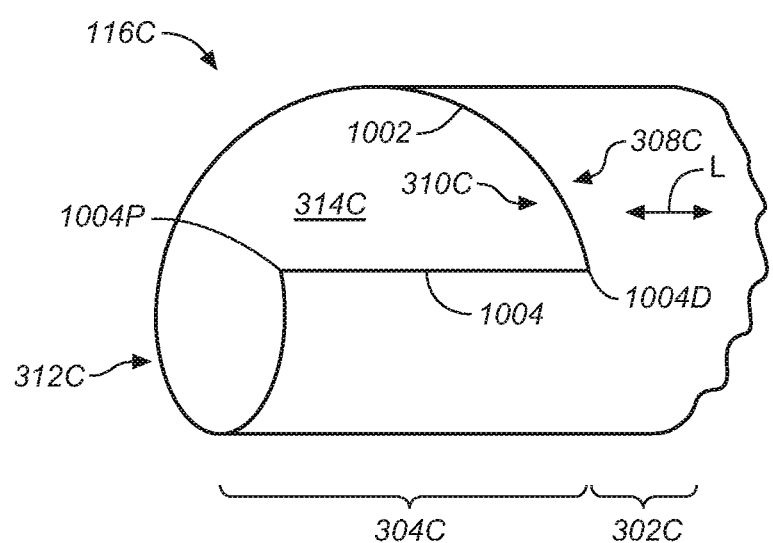

FIG. 10 is an oblique view of a control release sleeve 116C in accordance with yet another example. Referring now to FIG. 10, control release sleeve 116C includes a cylindrical wall portion 302C and a control release portion 304C. Cylindrical wall portion 302C is similar to cylindrical wall portion 302 of control release sleeve 116 as discussed above and so is not repeated here.

Control release portion 304C is connected to and extends proximally from a proximal end 308C of cylindrical wall portion 302C. More particularly, a distal end 310C of control release portion 304C is connected to proximal end 308C of cylindrical wall portion 302C. Control release portion 304C extends proximally from distal end 310C to a proximal end 312C of control release portion 304C.

Control release portion 304C is generally cylindrical but includes a variable size opening 314C, sometimes called a variable size space, within control release sleeve 116C. Stated another way, control release portion 304C is a hollow cylinder, except has a portion of the cylinder cutaway thus forming variable size opening 314C. Accordingly, variable size opening 314C is sometimes called a cutaway portion of the cylinder of control release portion 304C and control release portion 304C is sometimes called a partially cutaway cylinder.

Variable size opening 314C is defined by a right hand helical edge 1002 and a longitudinal edge 1004. Longitudinal edge 1004 is parallel to longitudinal axis "L" of control release portion 304C. Longitudinal edge 1004 has a proximal end 1004P at proximal end 312C of control release portion 304C and a distal end 1004D at distal end 310C of control release portion 304C.

Right hand helical edge 1002 extends between proximal end 1004P and distal end 1004D of longitudinal edge 1004. Right hand helical edge 1002 is a right hand helix.

Accordingly, variable size opening 314C is larger at proximal end 312C than at distal end 310C between longitudinal edge 1004 and right hand helical edge 1002 and so is called a variable size opening.

Control release portion 304C is defined by right hand helical edge 1002 and longitudinal edge 1004.

In a manner similar to that discussed above in reference to FIGS. 5, 6, 7, as control release sleeve 116C is advanced, right hand helical edge 1002 is sequentially advanced beyond spindle pins 132 thus releasing the respective proximal apexes 506 until all proximal apexes 506 have been released. More particularly, proximal apexes 506 are released radially sequentially counterclockwise when viewed in the distal direction (when viewed from the handle), i.e., one at a time in a counterclockwise circumferential direction. In this manner, sequential controlled releases of proximal apexes 506 is achieved. In one example, the pitch of right hand helical edge 1002 is varied to obtain a desired release timing of proximal apexes 506.

In one example, the various edges of control release sleeves as set forth above in the examples of FIGS. 1-10 are rounded and thus designed to be atraumatic. For example, the edges are rounded to minimize potential snagging on tip recapture and/or on delivery system withdrawal.

Figure 11:
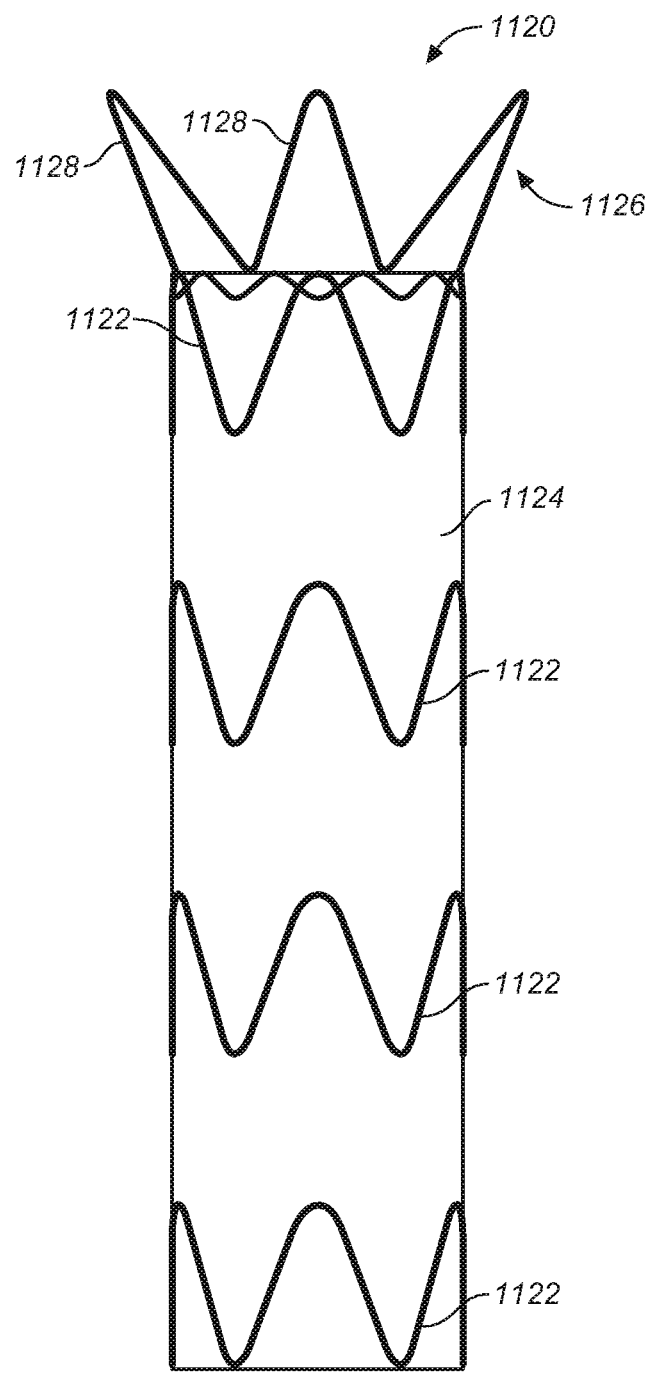
FIG. 11 is a side view of a stent graft.

FIG. 11 is a side view of a stent graft for use with a stent graft delivery system. The stent graft 1120, illustrated in the deployed state, includes stent 1122s and graft material 1124 supported by the stents 1122. In this example, the stent graft 1120 further includes a bare stent (spring) 1126, sometimes called a proximal anchor stent ring, with a number of bare stent crowns 1128, sometimes called proximal apexes. The bare stent 1126 extends beyond the graft material 1124 to provide a radial force which engages the vessel wall and seals the stent graft 1120 at the vessel wall. One apex of each stent crown 1128 is at the end of the stent graft 1120. In another embodiment, the bare stent can be omitted. The stent graft 1120 is delivered to the deployment site at a delivery diameter and expanded at the deployment site to a deployed diameter.

A stent graft can be described as any suitable device for mechanically keeping a tubular graft open and in sealing contact with healthy surrounding tissue after being implanted at the deployment site, such as a deployment site in the abdominal aorta, thoracic aorta, or other vessel. Such mechanical endoprosthetic devices are typically inserted into the target vessel, positioned across the lesion, and then expanded to bypass the weakened wall of the vessel, thereby preventing rupture of the aneurysm. The stent graft is in contact with the healthy tissue after implantation of the stent graft. The stent graft generally extends across the aneurysm in a vessel to divert flow through the stent graft and relieve the pressure normally applied to the weak aneurysmal wall.

The size and configuration of the stents 1122 depend upon the size and configuration of the vessel to be treated. Individual stents 1122 can be connected to each other by articulated or rigid joints or can be attached only to the graft material 1124. The minimum length of the stent graft 1120 to be used is matched (slightly oversized) to the size of the aneurysm across which the stent graft 1120 will be implanted.

The stents 1122 and the graft material 1124 can be any stents and the graft material typically used for stent grafts. The stents 1122 can be self-expanding or balloon expandable, and can be a single unit along the whole length of the stent graft or a series of individual stents as illustrated in FIG. 11. The stents 1122 can be made of can be made of spring steel, stainless steel, titanium, nickel titanium alloys (Nitinol), a polymer or copolymer, a combination of these materials, or other suitable materials. The graft material 1124 can be any woven or interlocked graft material suitable for stent grafts, such as woven polymer materials, e.g., Dacron polyester, or polytetrafluoroethylene (PTFE), or interlocked graft materials including knit, stretch, and velour materials. In some embodiments, the graft material 1124 includes components made of collagen, albumin, an absorbable polymer, or biocompatible fiber. Alternatively, the graft material 1124 is constructed from one or more suitable metallic, plastic, or non-biodegradable materials.

Figure 12:
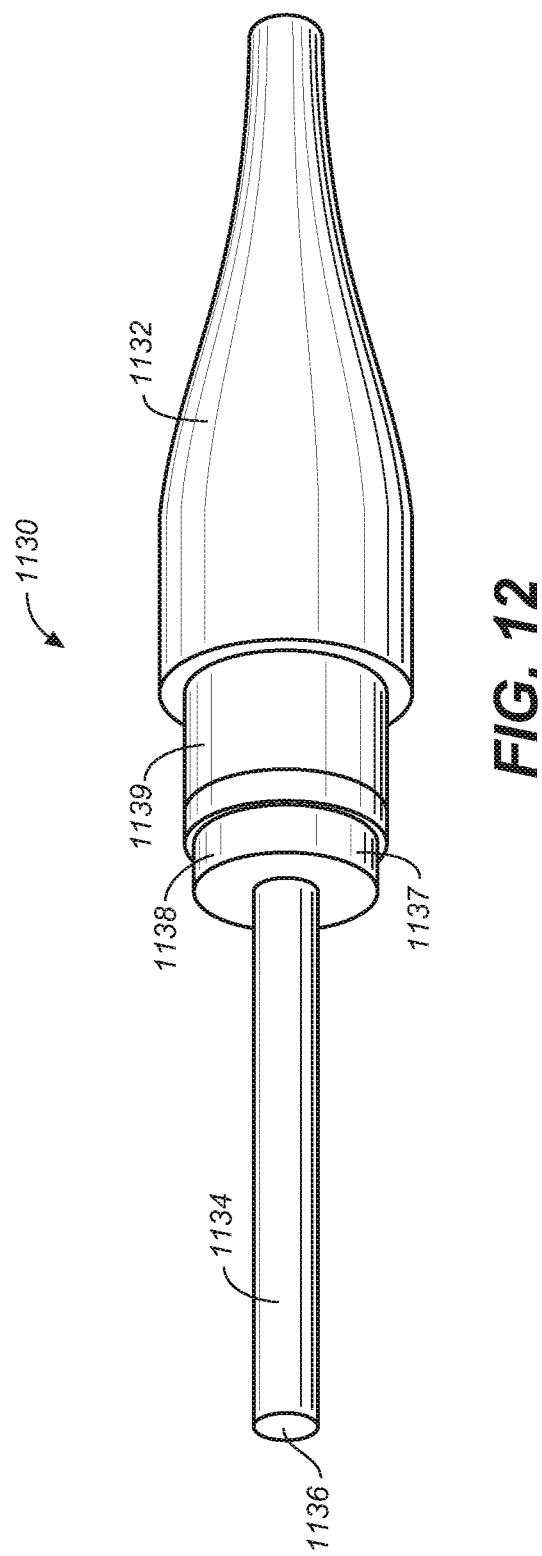
FIG. 12 is a perspective view of a portion of a nosecone assembly.

FIGS. 12-14 illustrate the parts of a stent graft delivery system. The stent graft delivery system includes a nosecone assembly, a spindle assembly, and a stent capture assembly. The nosecone assembly has a nosecone and a nosecone shaft, with a nosecone assembly lumen therethrough through which a guidewire can slide. The spindle assembly has a spindle fitting and a spindle shaft, with a spindle assembly lumen therethrough through which the nosecone shaft can slide. The stent capture assembly has a stent capture fitting and a stent capture shaft, and defines a stent capture assembly lumen through which the spindle shaft can slide. The spindle fitting and the stent capture fitting are slidably mateable and releasably retain the proximal end of the stent graft at a (compressed) delivery diameter. The spindle fitting, the stent capture fitting, and the nosecone can each move independently and relative to each other, although when moved toward each other and into contact with the adjacent piece, the pieces in contact will move as one. When the spindle fitting engages the stent graft bare spring, the spindle fitting motion is limited by the travel limits imposed by the bare stent, the nosecone and capture fittings. The stent capture fitting can be retracted from the spindle fitting to release the end of the stent graft or the nosecone assembly can be disengaged from the spindle assembly to release the end of the stent graft.

FIG. 12 is a perspective view of a portion of a nosecone assembly. The nosecone assembly 1130 includes a nosecone 1132 and a nosecone shaft 1134, and guides the spindle assembly and stent capture assembly through the vasculature. The nosecone 1132 can be generally tapering from the distal to the proximal end to facilitate passage through a vessel. The nosecone shaft 1134, which guides the spindle fitting and stent capture fitting to the deployment site, is long enough the reach through the vasculature from the stent graft deployment site in the vessel to the clinician. The proximal end of the nosecone shaft 1134 can be attached to a handle (not shown) for manipulation by the clinician during stent graft delivery. In one embodiment, the nosecone assembly 1130 defines a guidewire lumen 1136 along its length through which a guidewire can slide to guide the delivery system to the deployment site. In another embodiment, the nosecone assembly 1130 can include a transition piece 1138 adapted to the spindle fitting and the stent capture fitting to assist in retaining one end of the stent graft and facilitate passage through the vasculature. The transition piece 1138 can include one or more steps in diameter. The transition piece 1138 can include an arm transition segment 1137, so that the arms of the stent capture fitting (not shown) can fit around the arm transition segment 1137. The diameter of the arm transition segment 1137 is sized to receive the stent capture fitting arms and to be smaller than the largest diameter of the nosecone 1132 so that the stent capture fitting arms are recessed and protected when passing through the vasculature. The transition piece 1138 can also include a catheter transition segment 1139, so that a catheter (not shown) can fit around the catheter transition segment 1139. The diameter of the catheter transition segment 1139 can be selected to match the inner diameter of the catheter, so that the catheter and the nosecone 1132 form a smooth profile when passing through the vasculature. In another embodiment, the transition piece can be omitted.

Those skilled in the art will appreciate that the nosecone assembly 1130 can made of any biocompatible material and can be formed as a single unit and/or assembled from individual parts. The nosecone 1132 can be constructed by insert molding the specific geometry of the nosecone 1132 over the nosecone shaft 1134. The nosecone material can be an elastomeric material of a specific durometer to provide a flexible tip for the stent graft delivery system. Suitable nosecone materials include Pebax, urethane, silicone, other flexible polymers, and the like. The nosecone 1132 may also include a radiopaque additive to provide the clinician with a visible tip when using fluoroscopy guidance to deliver the stent graft within the patient.

Figures 13A, 13B, 13C:
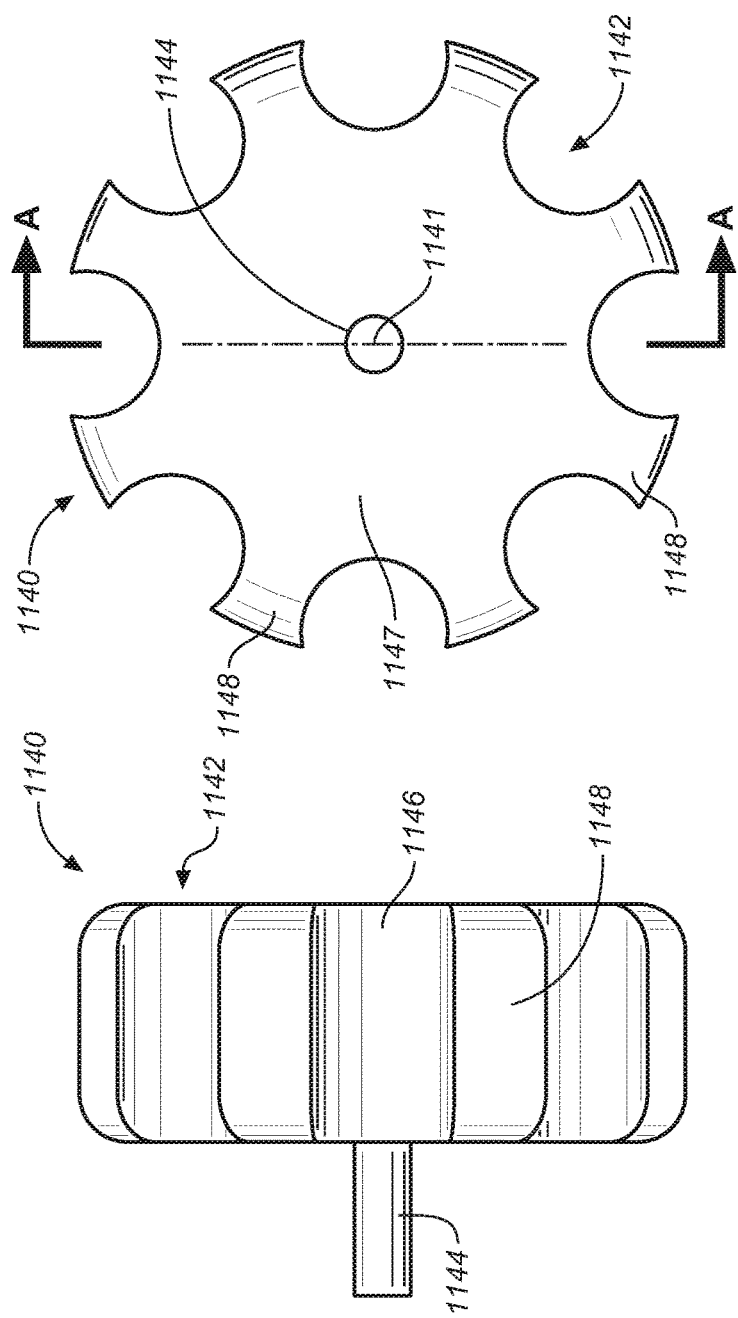
FIGS. 13A & 13B are a side and end view, respectively, of a portion of a spindle assembly.
FIG. 13C is a side view of another embodiment of a spindle fitting.

FIGS. 13A & 13B are a side and end view, respectively, of a portion of a spindle assembly. The spindle assembly 1140 includes a spindle fitting 1142 and a spindle shaft 1144. The spindle assembly 1140 defines a spindle assembly lumen 1141 along its length through which the nosecone shaft (not shown) can slide. The diameter of the spindle assembly lumen 1141 is large enough that the nosecone shaft (not shown) can slide within the spindle assembly lumen 1141. The spindle shaft 1144 advances the spindle fitting 1142 over the nosecone shaft to the deployment site. The spindle shaft 1144 is long enough the reach through the vasculature from the stent graft deployment site in the vessel to the clinician. The proximal end of the spindle shaft 1144 can be attached to a handle (not shown) for manipulation by the clinician during stent graft delivery. Those skilled in the art will appreciate that the spindle assembly 1140 can made of any biocompatible material and can be formed as a single unit and/or assembled from individual parts. The spindle shaft can be constructed of a rigid plastic such as PEEK polyetheretherketone, polyimide, nylon, or the like. The spindle shaft can alternatively be constructed of a flexible metal tube such as nitinol, stainless steel, or the like.

The spindle fitting 1142, in cooperation with the stent capture fitting (not shown), retains one end of the stent graft during stent graft delivery. In the illustrated embodiment, the spindle fitting 1142 includes a spindle body 1147 and a number of spindle pins 1148 disposed around the circumference of the spindle body 1147. A spindle groove 1146 is formed between each pair of adjacent spindle pins 1148. A single stent crown (not shown) wraps around each spindle pin 1148 and is held in place by a stent capture fitting arm (not shown) during stent graft delivery. When the stent capture fitting is retracted, the stent crowns are freed from the spindle pins 1148 and the stent crown expands into position in the vessel. The spindle fitting 1142 can be made of any rigid and/or compliant biocompatible material and can be formed as a single unit and/or assembled from individual parts. The spindle fitting can be fabricated from a variety of materials. This may include rigid plastic materials such as PEEK polyetheretherketone, polycarbonate, or the like, and may also include metals such as stainless steel. In one embodiment, a hard plastic is desirable for the spindle fitting to avoid damage to the stent surface, which is in contact with the spindle fitting. The spindle fitting can be fastened to the spindle shaft by bonding the two with adhesive or threading the two components together. The spindle fitting may alternatively be insert molded directly on the spindle shaft.

FIG. 13C is a side view of another embodiment of a spindle fitting. In this embodiment, each of the spindle pins 1148-1 on the spindle body 1147 includes a spindle slot 1149 along the spindle pin circumference of the spindle pins 1148-1. The spindle pin circumference is defined by the ends of the spindle pins 1148-1 away from the spindle body. The distal end of each stent crown, i.e., the apex of each bare stent, rests in one of the spindle slots 1149 and the stent capture fitting arm retains the stent crown in the spindle slot 1149. The stent capture fitting positively retains the stent crown in the spindle slot 1149 until the stent capture fitting is retracted.

In another embodiment, the spindle fitting can be a compliant disc of a uniform circumference and omitting the spindle pins. The stent crowns can be pressed into the compliant disc by the stent capture fitting arm to hold the stent crown compressed during stent graft delivery. When the stent graft does not include a bare stent, the stent capture fitting arms can press the distal end of the stent graft (both the stent and the graft material) into the compliant disc. The graft material can be stretchable or loose on the stents to allow the graft material to extend around the stent capture fitting arms when the stent capture fitting arm holds the distal end of the stent compressed. The compliant disc can be made of a low durometer polymer such as silicone. In yet another embodiment, the spindle fitting can be molded to include additional features that match the specific shape of the compressed stent. In one example, the spindle pins may have a tapered profile that matches the curvature of the compressed stent crown.

FIGS. 14A & 14B are a side and end view, respectively, of a portion of a stent capture assembly. The stent capture assembly 1150 includes a stent capture fitting 1152 and a stent capture shaft 1154. The stent capture assembly 1150 defines a stent capture assembly lumen 1156 along its length through which the spindle shaft (not shown) can slide. The diameter of the stent capture assembly lumen 1156 is large enough that the spindle shaft (not shown) can slide within the stent capture assembly lumen 1156. The stent capture shaft 1154 advances the stent capture fitting 1152 to the deployment site and retracts the stent capture fitting 1152 to release the end of the stent graft from the delivery diameter. The stent capture shaft 1154 is long enough the reach through the vasculature from the stent graft deployment site in the vessel to the clinician. The proximal end of the stent capture shaft 1154 can be attached to a handle (not shown) for manipulation by the clinician during stent graft delivery. Those skilled in the art will appreciate that the stent capture assembly 1150 can made of any biocompatible material and can be formed as a single unit and/or assembled from individual parts. The stent capture shaft may be constructed of a rigid plastic, such as PEEK polyetheretherketone, polyimide, nylon, or the like. The stent capture shaft can alternatively be constructed of a flexible metal tube such as nitinol, stainless steel, or the like.

The stent capture fitting 1152, sometimes called a control release sleeve, in cooperation with the spindle fitting (not shown), retains one end of the stent graft during stent graft delivery. In the illustrated embodiment, the stent capture fitting 1152 includes a stent capture body 1157 having a number of stent capture fitting arms 1158, disposed around the circumference of the stent capture body 1157. The stent capture body 1157 defines a number of stent capture grooves 1159 between each of the stent capture fitting arms 1158 to receive the bare stent crowns. The stent capture fitting arms 1158 can be substantially parallel to the central axis of the stent capture fitting 1152, i.e., the axis along the stent capture shaft 1154. In other embodiments, the stent capture fitting arms 1158 can curve toward or away from the axis of the stent capture fitting 1152 as desired for a particular purpose.

As illustrated in FIG. 14A, one or more of stent capture fitting arms 1158, e.g., stent capture fitting arm 1158A of stent capture fitting arms 1158, is shorter than one or more of the other stent capture fitting arms 1158. To illustrate, stent capture fitting arm 1158A is shorter than a second stent capture fitting arm 1158B of capture fitting arms 1158.

More particularly, stent capture fitting arm 1158A has a circumferential edge 1316 at a distal end of stent capture fitting arm 1158A. In accordance with this embodiment, the other longer stent capture fitting arms 1158 including stent capture fitting arm 1158B have circumferential edges 1322 at distal ends of the stent capture fitting arms 1158. Circumferential edges 1322 of the longer stent capture fitting arms 1158 are distal to circumferential edge 1316 of stent capture fitting arm 1158A. Thus, prior to retraction of stent capture fitting 1152 relative to spindle pins 1148, a first distance between the respective spindle pin 1148 and circumferential edge 1316 in a direction parallel to longitudinal axis "L" is less than a second distance between the respective remaining spindle pins 1148 and circumferential edges 1322.

When the stent capture fitting 1152 is retracted, the stent capture fitting arms 1158 release the bare stent crowns, and the bare stent crowns expand into position in the vessel. More particularly, as circumferential edge 1316 of stent capture fitting arm 1158A is retracted past the respective bare stent crown, the bare stent crown is exposed and release. However, circumferential edges 1322 are not retracted past the remaining respective bare stent crowns, but remain distal thereto as discussed further below. Accordingly, these remaining respective bare stent crowns remain retained by the stent capture fitting arms 1158.

To release these remaining respective bare stent crowns, stent capture fitting 1152 is further retracted. This causes circumferential edges 1322 of stent capture fitting arms 1158 to be retracted past the respective bare stent crown, and the bare stent crowns are exposed and release.

Although stent capture fitting 1152 is illustrated as having stent capture fitting arms 1158 with two lengths, e.g., short stent capture fitting arm 1158A and the remaining long stent capture fitting arms 1158 including stent capture fitting arm 1158B, in other examples, similar stent capture fittings include several variable length stent capture fitting arms to sequentially release the bare stent crowns in the order desired.

The stent capture fitting 1152 can be made of any rigid and/or compliant biocompatible material and can be formed as a single unit and/or assembled from individual parts. The stent capture fitting may be fabricated from a variety of materials. This may include rigid plastic materials such as PEEK polyetheretherketone, polycarbonate, or the like, and may also include metals such as stainless steel. In one embodiment, a hard plastic or highly polished metal is desirable for the stent capture fitting to avoid damage to the stent surface which is in contact with the stent capture fitting. The stent capture fitting can be fastened to the stent capture shaft by bonding the two with adhesive or threading the two components together. The stent capture fitting may alternatively be insert molded directly on the stent capture shaft.

FIG. 14C is a side view of another embodiment of a stent capture fitting arm. The distal end of each of the stent capture fitting arms 1158 can include a protrusion 1153 projecting inwardly toward the central axis of the stent capture fitting. The protrusions 1153 can be large enough to positively retain the distal end of the bare stent crown on the stent capture fitting arm, but small enough to allow the stent capture fitting arm 1158 to be retracted over the distal end of the bare stent crown.

Figure 15A:
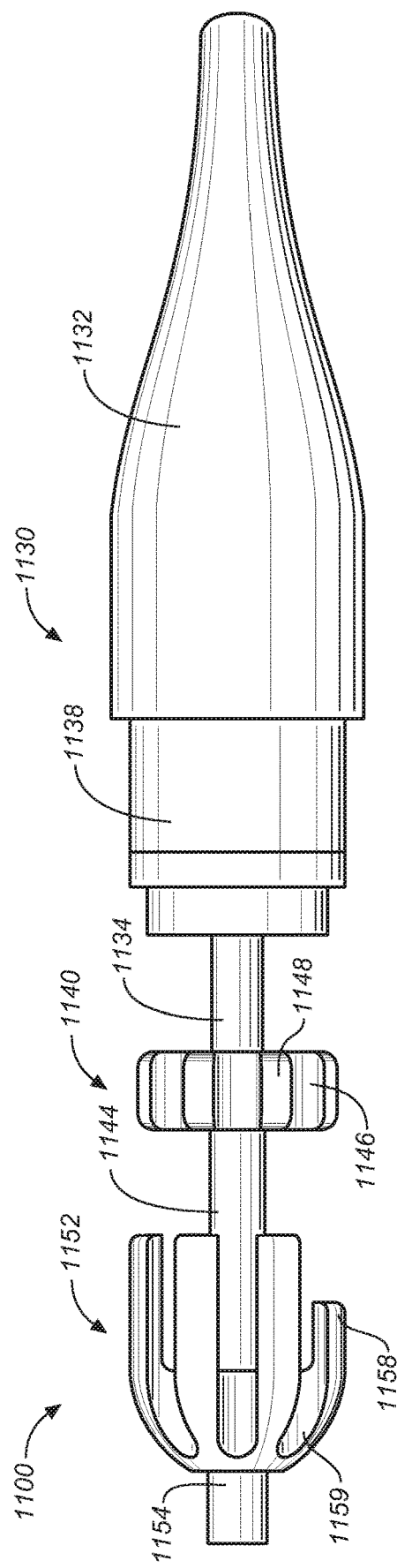
FIGS. 15A & 15B are a side view and perspective view, respectively, of a portion of a stent graft delivery system.
Figure 15B:
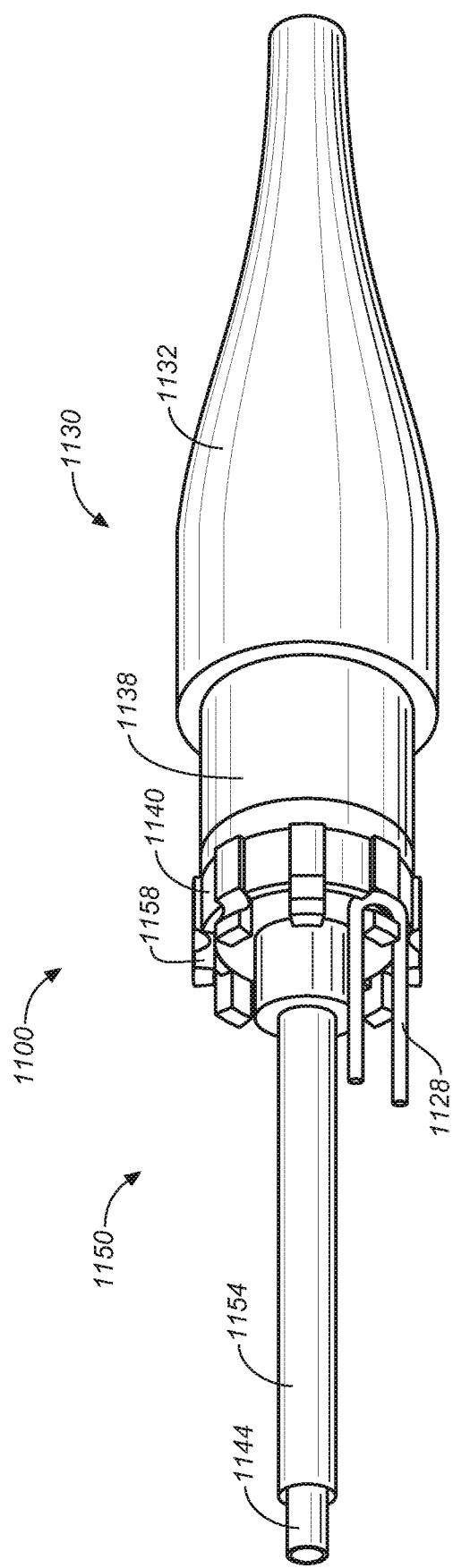

FIGS. 15A & 15B are a side view and a partial perspective view, respectively, of a portion of a stent graft delivery system. FIG. 15A illustrates the stent graft delivery system components slid apart in preparation for loading a stent graft and FIG. 15B illustrates the components slid together. FIG. 15B shows one bare stent crown 1128 in the loaded position and omits the remainder of the stent graft for clarity of illustration. The stent graft delivery system 1100 includes nosecone assembly 1130, spindle assembly 1140, and stent capture assembly 1150. The spindle assembly 1140 is slidably disposed over the nosecone shaft 1134 of the nosecone assembly 1130 and the stent capture assembly 1150 is slidably disposed over the spindle shaft 1144. In this example, the stent capture fitting arms 1158 of the stent capture fitting 1152 extend onto the transition piece 1138 of the nosecone assembly 1130. Those skilled in the art will appreciate that the stent capture fitting arms 1158 only need extend far enough to secure the stent crowns 1128 on the spindle assembly 1140 and need not extend onto the transition piece 1138. For example, stent capture fitting arm 1158A does not extend onto the transition piece 1138 in one example while the remaining stent capture fitting arms 1158 do extend onto the transition piece 1138. In other examples, stent capture fitting arm 1158A and the remaining stent capture fitting arms 1158 all extend onto the transition piece 1138, or alternatively, do not extend onto the transition piece 1138.

The proximal ends of the nosecone assembly 1130, spindle assembly 1140, and stent capture assembly 1150 can terminate in a handle which allows the clinician to slide each of the shafts independently of each other and to advance the shafts through the vasculature as a group. The stent graft delivery system 1100 can also include a graft cover (or sheath) (not shown) slidable over the stent capture assembly 1150 and the stent graft when the proximal end of the stent graft is retained between the spindle fitting 1142 and the stent capture fitting 1152. The graft cover can hold the stent graft at a compressed delivery diameter until deployed.

Figure 16A:
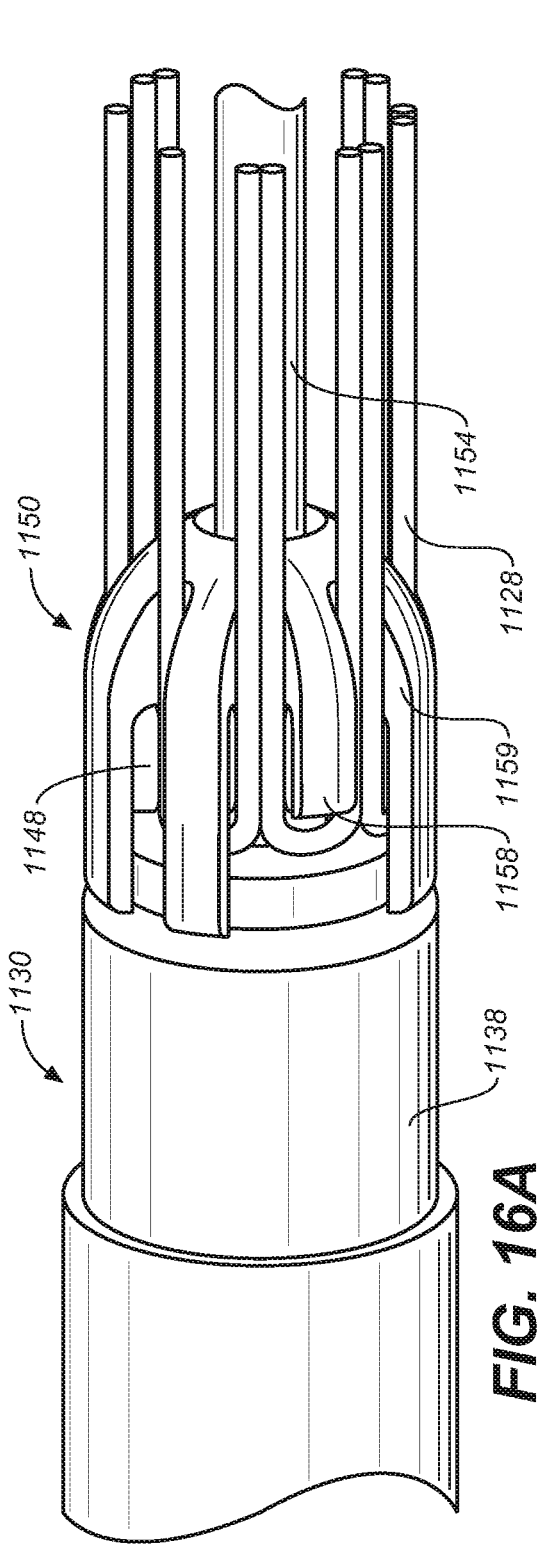
FIGS. 16A-16C are detailed perspective views of a portion of a stent graft delivery system.
Figure 16B:
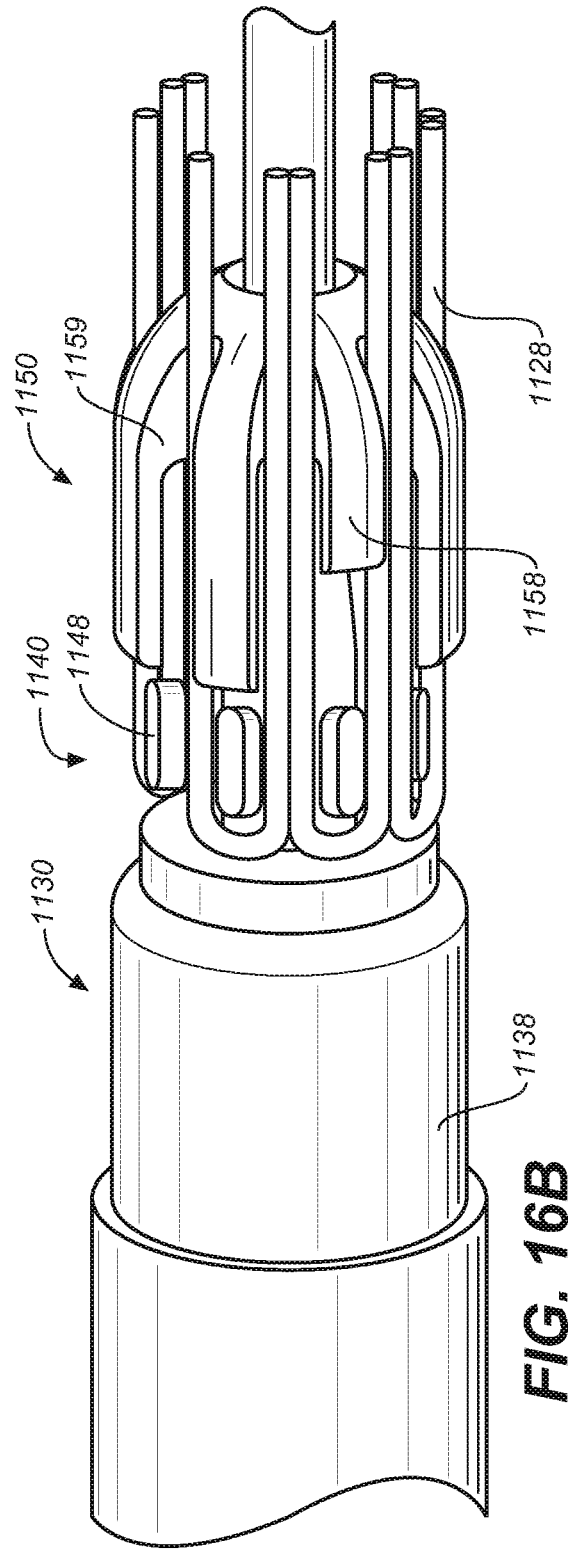
Figure 16C:
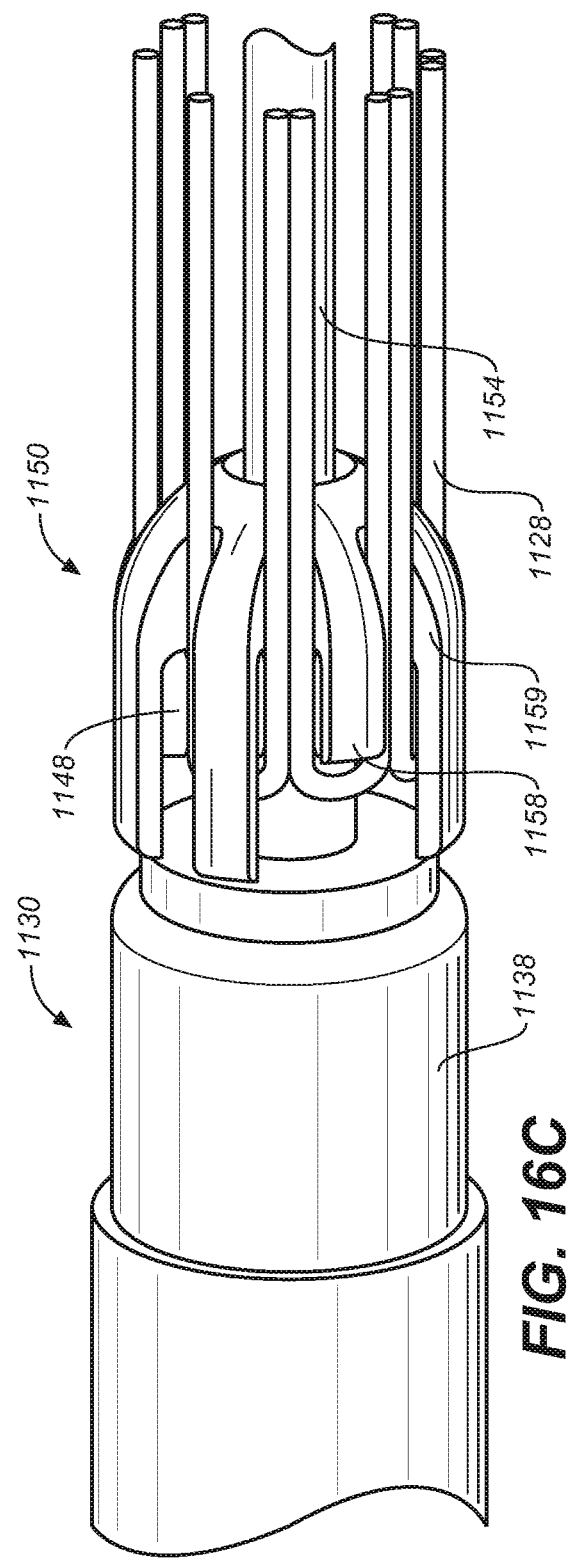

FIGS. 16A-16C are detailed perspective views of a portion of a stent graft delivery system. FIG. 16A illustrates the end of the stent graft retained between the spindle fitting and the stent capture fitting; FIG. 16B illustrates the stent capture fitting retracted from the spindle fitting; and FIG. 16C illustrates the nosecone pushed forward away from the spindle fitting and the stent capture fitting.

Referring to FIG. 16A, the stent graft is loaded in the stent graft delivery system, with the bare stent crowns 1128 about the spindle pins 1148 of the spindle fitting. The stent capture fitting arms 1158 extend through the grooves 1159 of the stent capture fitting 1152. In this example, the distal ends of the stent capture fitting arms 1158 extend onto the nosecone assembly 1130. The apex of each bare stent crown 1128 is trapped by the stent capture fitting arm 1158, the spindle pin 1148, and the arm transition segment 1137.

Referring to FIG. 16B, the stent capture fitting 1152 is illustrated in a retracted position, so that the stent capture fitting arms 1158 are withdrawn from the spindle pins 1148 of the spindle assembly 1140 and no longer positioned to trap the bare stent crowns 1128. The bare stent crowns 1128 are shown at the compressed delivery diameter for clarity of illustration, while actually the stent crowns 1128 when no longer trapped would have self expanded to the deployment diameter when the stent capture fitting 1152 was retracted and the stent graft is free of the graft cover.

Referring to FIG. 16C, the nose cone 1132 is pushed forward away from both the spindle fitting and the stent capture fitting 1152. The nosecone assembly, spindle assembly, and stent capture assembly are slidable independently of each other, so the position of the nose cone 1132 can be adjusted relative to the deployment site without moving spindle fitting and the stent capture fitting 1152. This allows deployment of the bare stent crowns by providing force on the nosecone shaft of the nosecone assembly when the stent capture fitting 1152 cannot be retracted from the spindle assembly 1140. The bare stent crowns 1128 exert an outward radial force against the distal ends of the stent capture fitting arms 1158 to hold the distal ends of the bare stent crowns 1128 at the delivery diameter until the nosecone is pushed forward to release the bare stent crowns.

Figure 17:
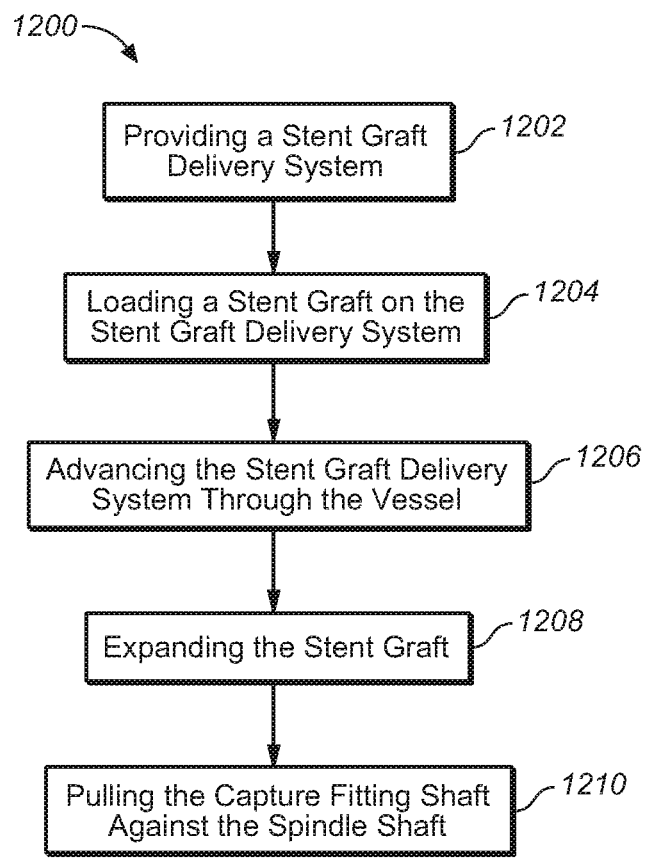
FIG. 17 is a flowchart of a method of delivering a stent graft to a deployment site in a vessel.

FIG. 17 is a flowchart of a method of delivering a stent graft to a deployment site in a vessel. The deployment site can be located in an abdominal aorta, a thoracic aorta, or any other vessel. The method 1200 includes the step of providing a stent graft delivery system (1202) including a nosecone assembly having a nosecone and a nosecone shaft; a spindle assembly having a spindle fitting and a spindle shaft the spindle assembly defining a spindle assembly lumen; and a stent capture assembly having a stent capture fitting and a stent capture shaft, the stent capture assembly defining a stent capture assembly lumen. The nosecone shaft is slidably disposed in the spindle assembly lumen and the spindle shaft is slidably disposed in the stent capture assembly lumen. The method 1200 further includes the steps of: loading a stent graft on the stent graft delivery system (1204) with one end of the stent graft over the spindle fitting, the stent capture fitting over the one end of the stent graft, and the stent graft compressed to a delivery diameter; advancing the stent graft delivery system through the vessel (1206) to align the spindle fitting with the deployment site; expanding the stent graft (1208) while maintaining the one end of the stent graft at the delivery diameter; and pulling the capture fitting shaft against the spindle shaft (1210) to retract the stent capture fitting and release the one end of the stent graft. In one embodiment, the nosecone assembly defines a guidewire lumen, and advancing the stent graft delivery system through the vessel (1206) includes advancing a guidewire through the vessel; inserting the guidewire in the guidewire lumen; and advancing the stent graft delivery system over the guidewire.

The stent capture assembly normally can be moved without applying any force to the nosecone assembly, but when the connection between the stent capture fitting and the deployment handle become inoperative (for whatever reason) the nosecone can be moved forward to effect deployment. Advancing the stent graft delivery system through the vessel (1206) can include sliding the stent capture assembly and the spindle assembly on the nosecone shaft until the spindle fitting is aligned with the deployment site. In one embodiment, the method 1200 can further include sliding the stent capture assembly and the spindle assembly on the nosecone shaft to realign the spindle fitting with the deployment site before pulling the capture fitting shaft relative to the spindle shaft to effect release of the bare stent crowns and the stent graft.

Figure 18:
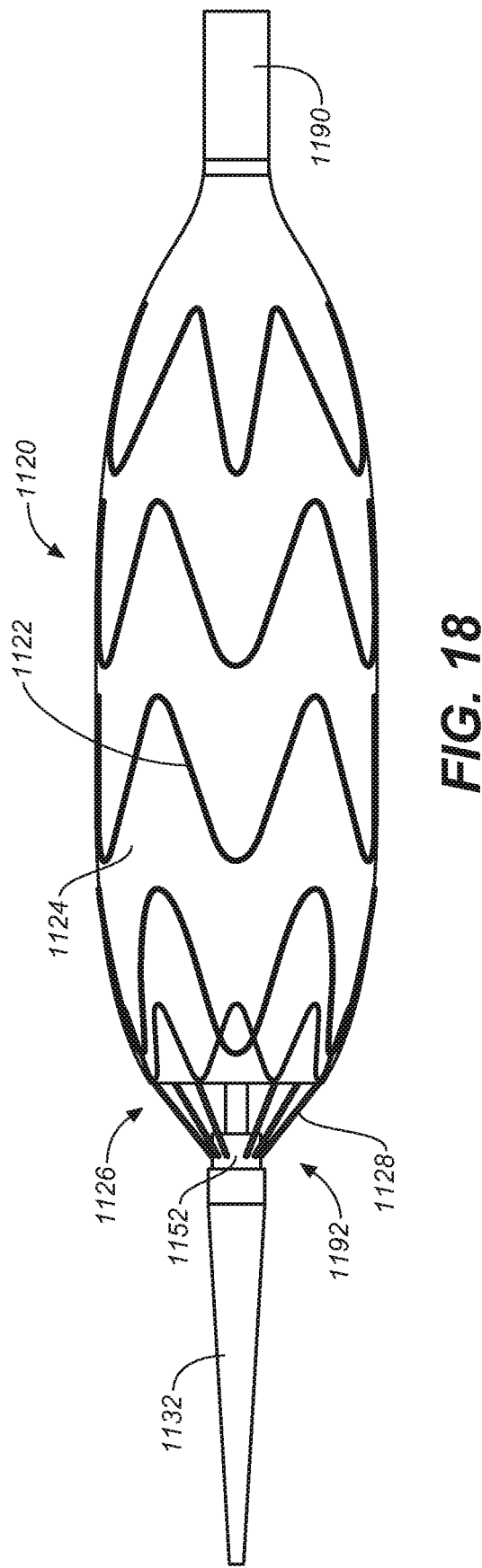
FIG. 18 is a schematicized side view of a partially deployed stent graft.

Expanding the stent graft (1208) while maintaining the proximal end of the stent graft the delivery diameter can includes retracting a graft cover 111190 to release the stent graft, as illustrated in FIG. 18.

FIG. 18 is a side view of a partially deployed stent graft. The graft cover 1190, sometimes called the primary sheath, is illustrated being retracted to release the stent graft 1120, which is expanding from a compressed delivery diameter to the expanded deployed diameter. The graft cover 1190 can releasably maintain the stent graft at the compressed delivery diameter for delivery through the vasculature. The distal end 1192 of the stent graft 1120 is retained at a delivery diameter by the stent capture fitting 1152. After the stent graft 1120 is free of the graft cover 1190 and the spindle fitting (not shown) is precisely aligned with the deployment site, the stent capture fitting 1152 can be retracted to release the distal end 1192 of the stent graft.

Figure 19A:
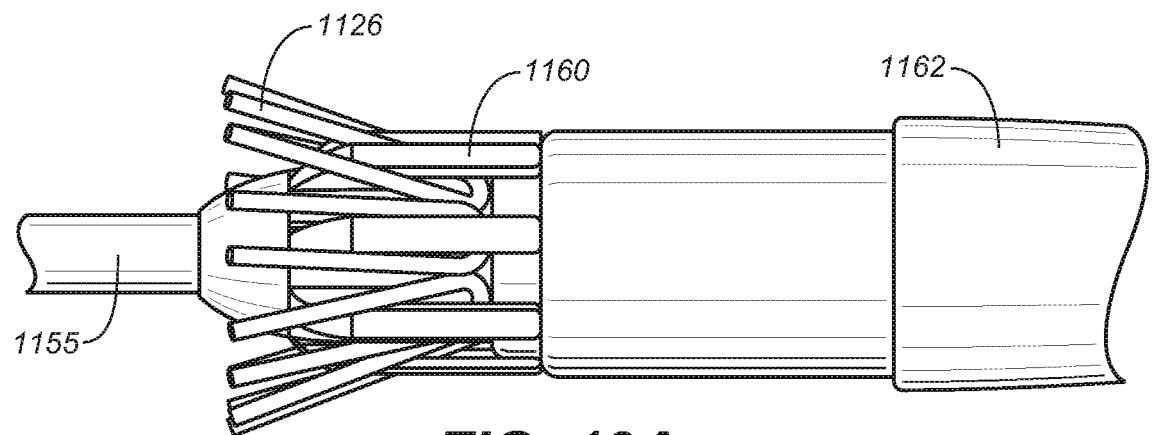
FIGS. 19A and 19B are partial and tight close-up plan views of another embodiment of a stent graft delivery system with a portion of the bare stent of the stent graft cut away for ease of understanding, where the crowns of the bare stent are captured by a stent graft capture fitting.
Figure 19B:
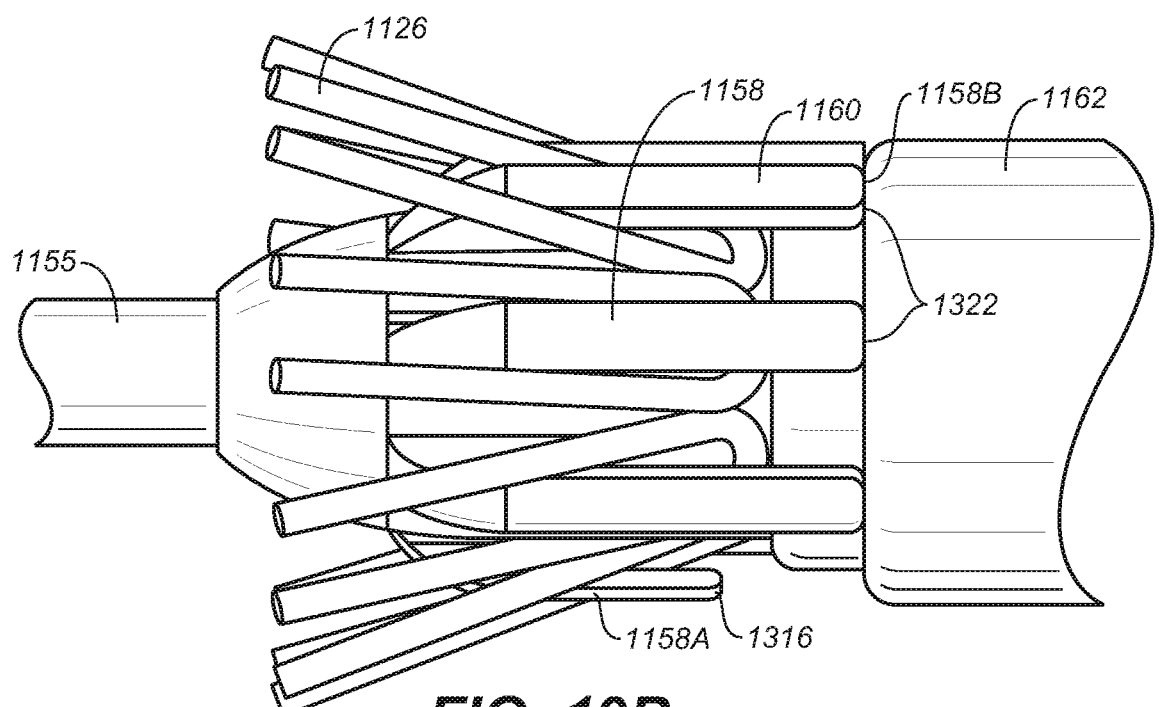

FIGS. 19A and 19B show a partial and tight plan views of an embodiment of a stent graft delivery system using only two longitudinally movable pieces, which move relative to one another. While the basic concept of two longitudinally movable pieces has been previously discussed, the details and execution disclosed herein are previously unknown. A nosecone shaft 1135 (not seen in FIGS. 19A and 19B) connects to a nosecone 1162. A stent capture shaft 1155 connected to a stent capture fitting 1160 surrounds the nosecone shaft 1135, thereby eliminating any stent crown escape gap therebetween, and is configured to slide relative to it as the stent capture fitting 1160 engages the nosecone 1162 and its spindle fitting 1143 (not seen in FIGS. 19A and 19B). The stent capture fitting 1160 includes stent capture fitting arms 1158 including stent capture fitting arms 1158A, 1158B as discussed above. Stent capture arm 1158A includes circumferential edge 1316 and the remaining stent capture arms 1158 including stent capture arm 1158B include circumferential edges 1322 as discussed above.

Figure 20A:
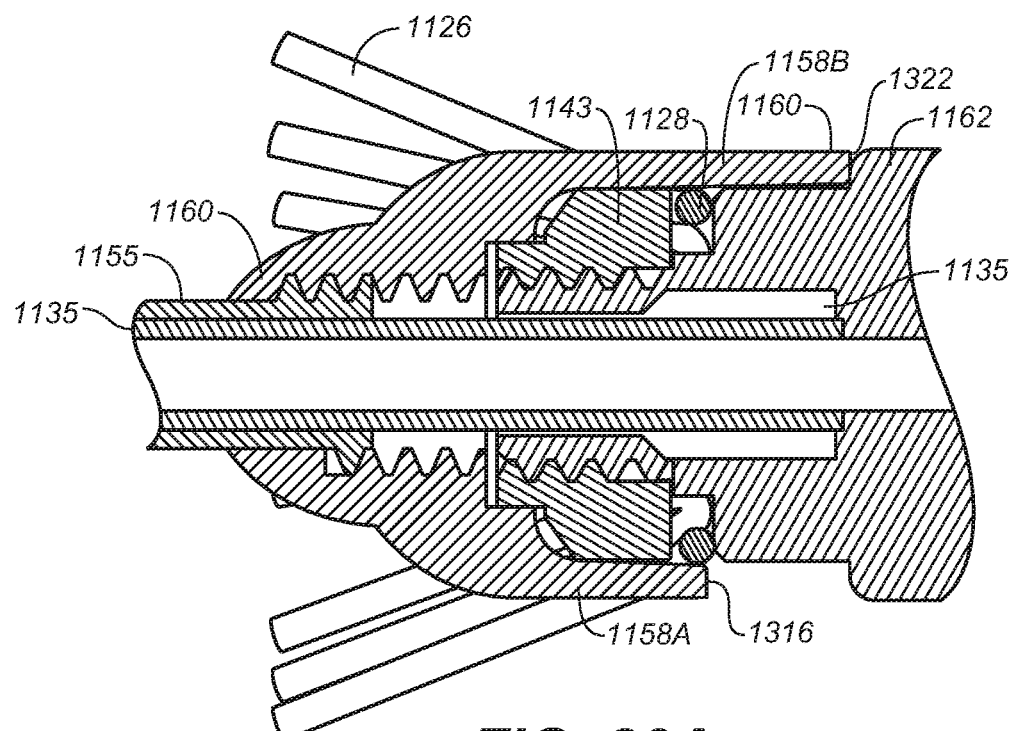
FIGS. 20A, 20B, 20C, and 20D are cross sectional views of the delivery system of FIGS. 19A and 19B showing progressive steps of stent graft deployment in a primary release mode.
Figure 20B:
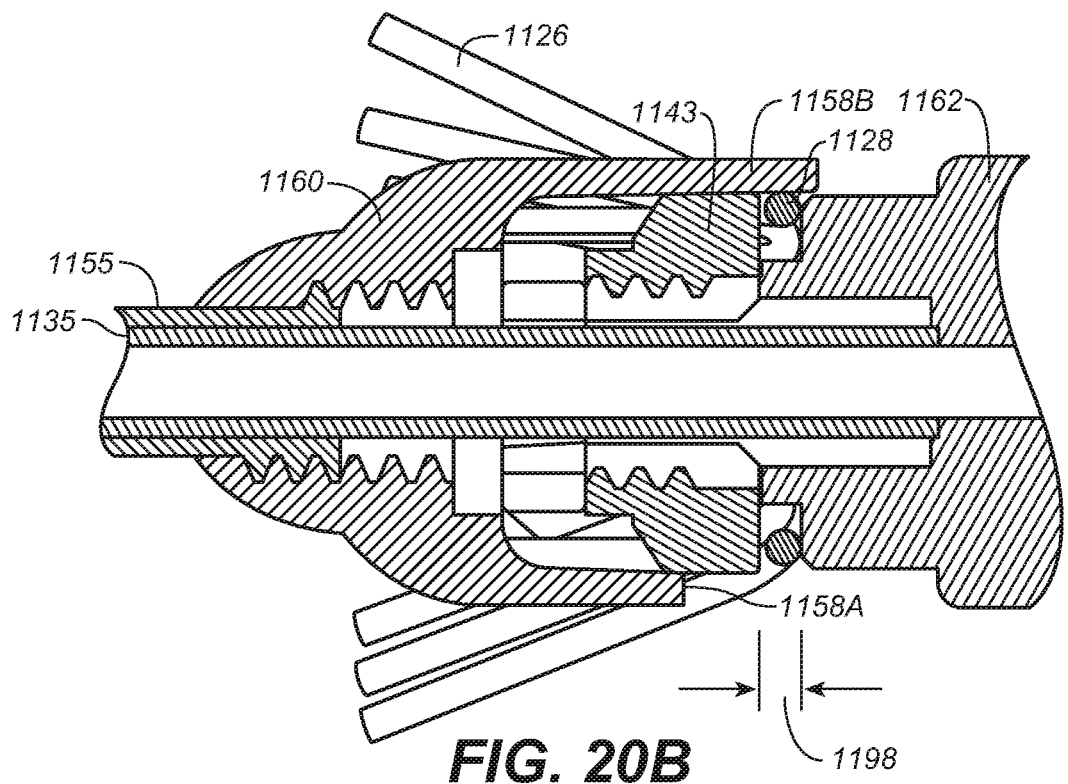
Figure 20C:
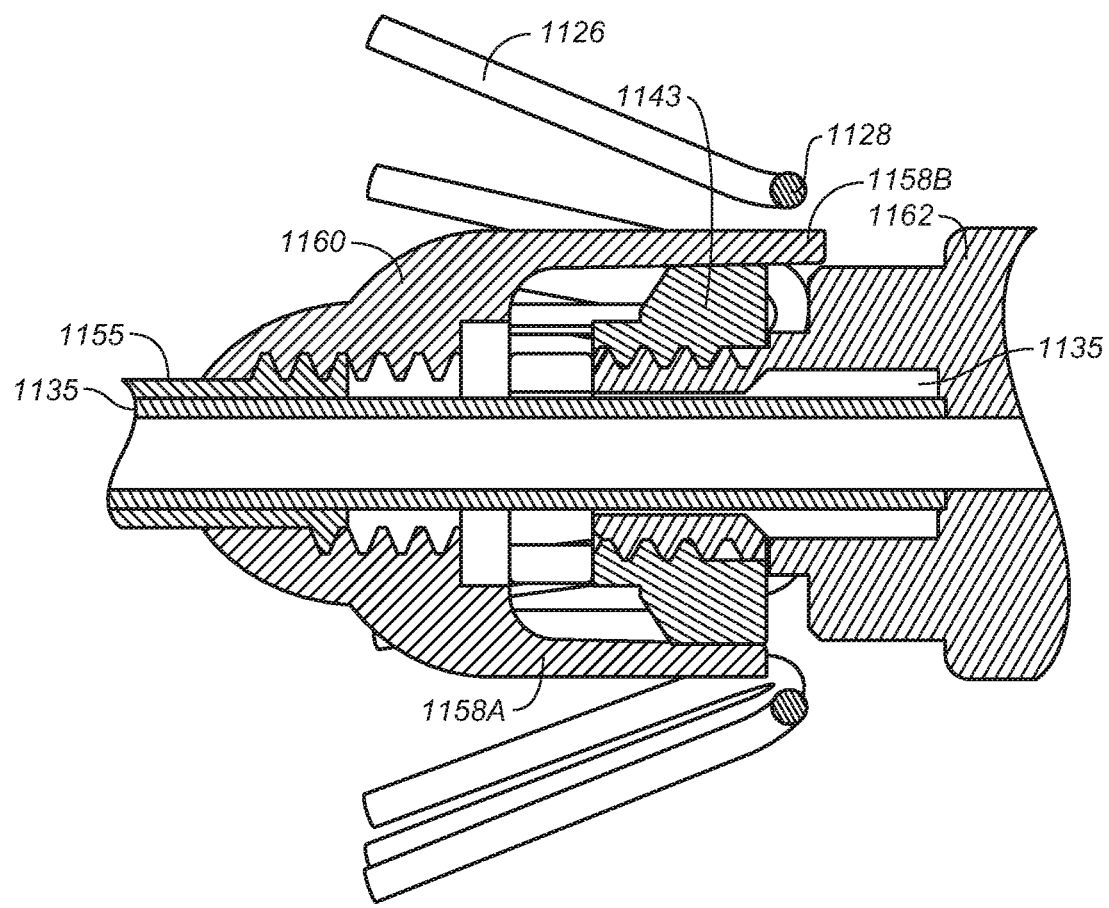

In viewing the cross section of the delivery system shown in FIGS. 20A, 20B, 20C, and 20D, the bare stent 1126 of the stent graft is cut away for clarity and the progressive views show a primary mode of deployment. The nosecone shaft 1135 has an integral bulb at it end to hold the nosecone 1162. The nosecone 1162 is over molded onto the nosecone shaft to form a unitary piece. A lower hub portion of the nosecone 1162 has threads formed on its outer surface. A spindle fitting 1143, having a similar perimeter configuration to the spindle fitting 1142, described in FIGS. 13A, 13B, and 13C, has a central opening having female threads configured to engage the threads on the lower hub of the nosecone 1162, such that when the threads of the spindle fitting 1143 and the threads of the nosecone 1162 are fully engaged, they together with the nosecone shaft 1135 move as one unitary piece. The stent capture shaft 1155 is at its end is threadably fixed to stent capture fitting 1160, and they move as a unitary piece. The stent capture fitting is configured substantially as previously described stent capture fitting 1152 in FIGS. 14A, 14B, and 14C. Thus in the primary mode of deployment, the two unitary pieces: the nosecone capture shaft 1135, the nosecone 1162, and the spindle fitting 1143; and the stent capture shaft 1155 and the stent capture fitting 1160 can move relative to one another longitudinally along the axis of the catheter. When the crown 1128 of the bare stent 1126 is captured by and between the top of the spindle fitting 1143, the bottom and outside of the nosecone 1162 across and adjacent to the spindle fitting 1143, and the inside of the stent capture fitting arms of the stent capture fitting 1160 to hold each of the crowns 1128 of the bare stent 1126 as the lower portion of the stent graft is deployed causing the struts of the bare stent 1126 to pivot around their captured crowns 1128 as is pictured in FIG. 20A. In the progression of the primary deployment mode, the lower portion of the stent graft having already been at least partially deployed to contact the adjacent vessel wall and become partially, if not fully, fixed at that particular deployment location in the vessel. The longitudinal position of the captured crowns is therefore substantially fixed within the limits of movement of the bare stent with respect to the main stent graft body portion to which it attaches. Once the stent graft has been partially deployed the crowns 1128 can no longer move longitudinally, they can only pivot outward. During primary deployment the stent capture shaft 1155 is pulled causing the stent capture fitting 1160 to be retracted and open a deployment gap 1198 (FIG. 20B) between the nosecone 1162 and the stent capture fitting arm 1158A of the stent capture fitting 1160 permitting the respective crown 1128 of the bare stent 1126 to pivot outward to complete deployment as seen in FIG. 20C. However, as further seen in FIG. 20C, the remaining crowns 1128 of the bare stent 1126 remain captured between the remaining stent capture fitting arms 1158 including stent capture fitting arm 1158B.

Figure 20D:
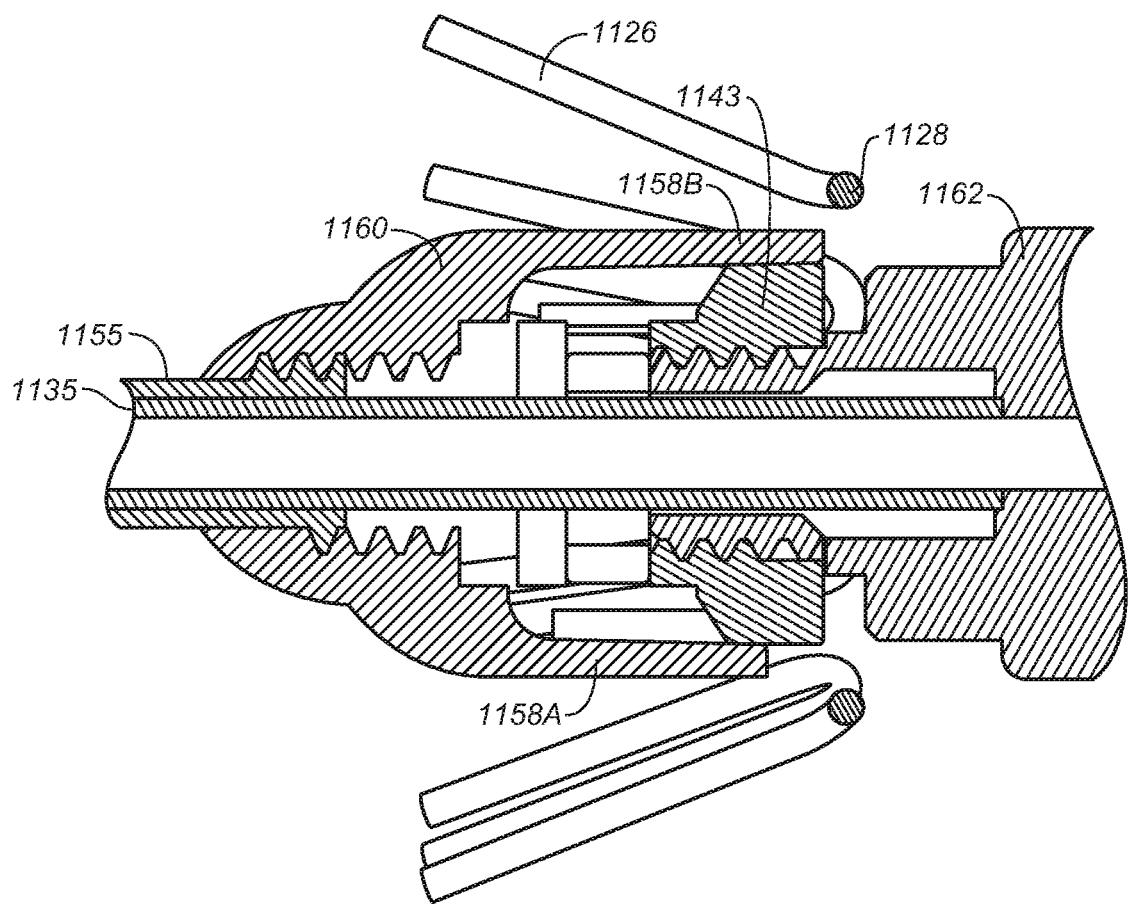

During further deployment, the stent capture shaft 1155 is further pulled causing the stent capture fitting 1160 to be retracted and open deployment gaps between the nosecone 1162 and the remaining stent capture fitting arms 1158 including stent capture fitting arm 1158B of the stent capture fitting 1160 permitting the respective crowns 1128 of the bare stent 1126 to pivot outward to complete deployment as seen in FIG. 20D.

However, when executing the steps of primary deployment FIGS. 20A, 20B, 20C, and 20D, it is possible that the connection from a catheter handle (not shown) to the stent capture shaft 1155 or that the stent capture shaft 1155 itself is broken such that longitudinal force cannot be exerted to retract the stent capture fitting 1160 to create the escape gaps shown in FIG. 20D. In the instance when the stent capture fitting 1160 is immovable, a one piece nosecone and spindle fitting as has been seen in the art would prevent the crowns 1128 of the bare stent form being deployed. Thus requiring an open surgical intervention to access the site to correct the situation by manual manipulation of the device to complete deployment, or removal of the device and implantation of a standard surgical graft with all the risks and complications associated with an open surgical procedure.

Figure 21A:
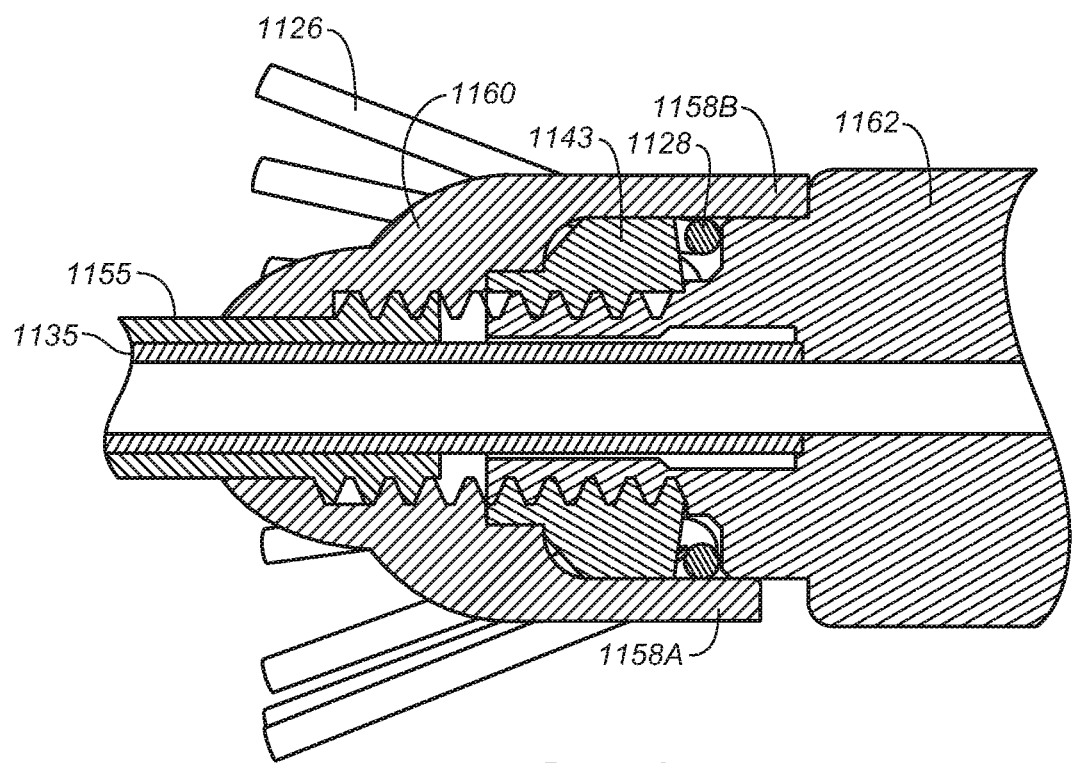
FIGS. 21A, 21B, 21C, and 21D are cross sectional views of the delivery system of FIGS. 19A and 19B showing progressive steps of stent graft deployment in a secondary release mode.
Figure 21B:
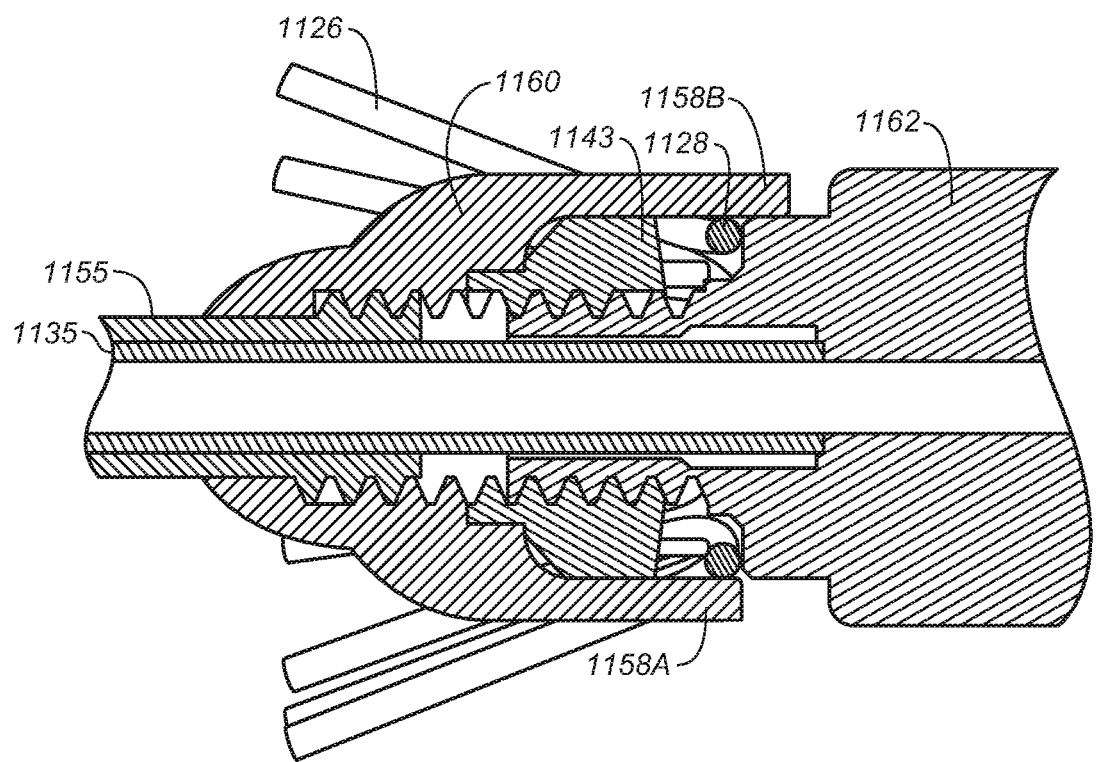
Figure 21C:
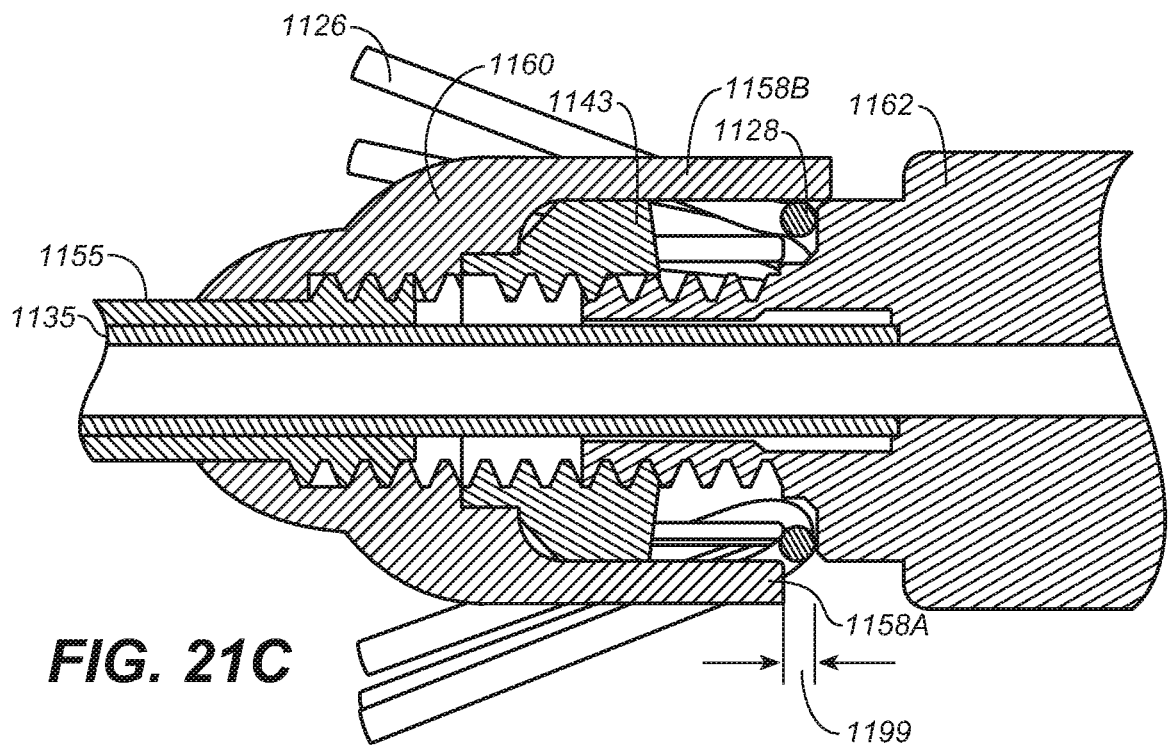

The device described here overcomes the failing of a one piece nosecone device. A secondary deployment procedure shown in FIGS. 21A, 21B, 21C, and 21D shows how the current device overcomes the above described deficiency. FIG. 21A shows the stent crown fully captured similar to that shown and described for FIG. 20A above. Upon the realization that the stent capture shaft 1155 cannot be retracted, the operator can initiate the secondary deployment procedure. The partially deployed stent graft in contact with the wall of the vessel acts as both a resistance or a substantial stop to longitudinal movement of the bare spring 1126 and also to rotational movement of the bare springs 1126. The crowns 1128 of the bare spring 1126 are positioned around the top of each pin of the spindle fitting 1143, which substantially prevents the longitudinal movement of the spindle fitting 1143 up or away from the stent graft, while the crowns 1128 are captured within the stent capture fitting 1160. However the threaded connection between the spindle fitting 1143 and the hub of the nosecone 1162, previously described, can used to separate the two. With the rotational position of the spindle fitting 1143 being set by its engagement with the bare stent which is substantially fixed to the wall of the surrounding vessel, as previously described, a rotational torque can be applied to the nosecone shaft 1135 to cause the nosecone 1162 to turn and separate from the spindle fitting 1143 by the longitudinal action of the threads as the nosecone is turned. This initiation of longitudinal movement of the nosecone 1162 away from the spindle fitting 1143 is shown in FIG. 21B. Because the bare stent 1126 has an unrestrained configuration that is approximately cylindrical, the crowns 1128 of the bare stent 1126 are urged outward and forward by internal forces which tend to return the bare stent 1126 to its unrestrained configuration. As the nosecone 1162 continues to be turned with respect to the spindle fitting 1143, as shown in FIG. 21C, a secondary deployment procedure gap 1199 between the nosecone 1162 and the spindle fitting 1143 (and also between the nosecone 1162 and the stent capture fitting arm 1158A of the stent capture fitting 1160) provides an opening allowing the respective crown 1128 of the bare stent 1126 to move forward and escape to provide full release of the crown 1128 of the bare stent 1126 as seen in FIG. 21C. However, as further seen in FIG. 21C, the remaining crowns 1128 of the bare stent 1126 remain captured between the remaining stent capture fitting arms 1158 including stent capture fitting arm 1158B.

Figure 21D:
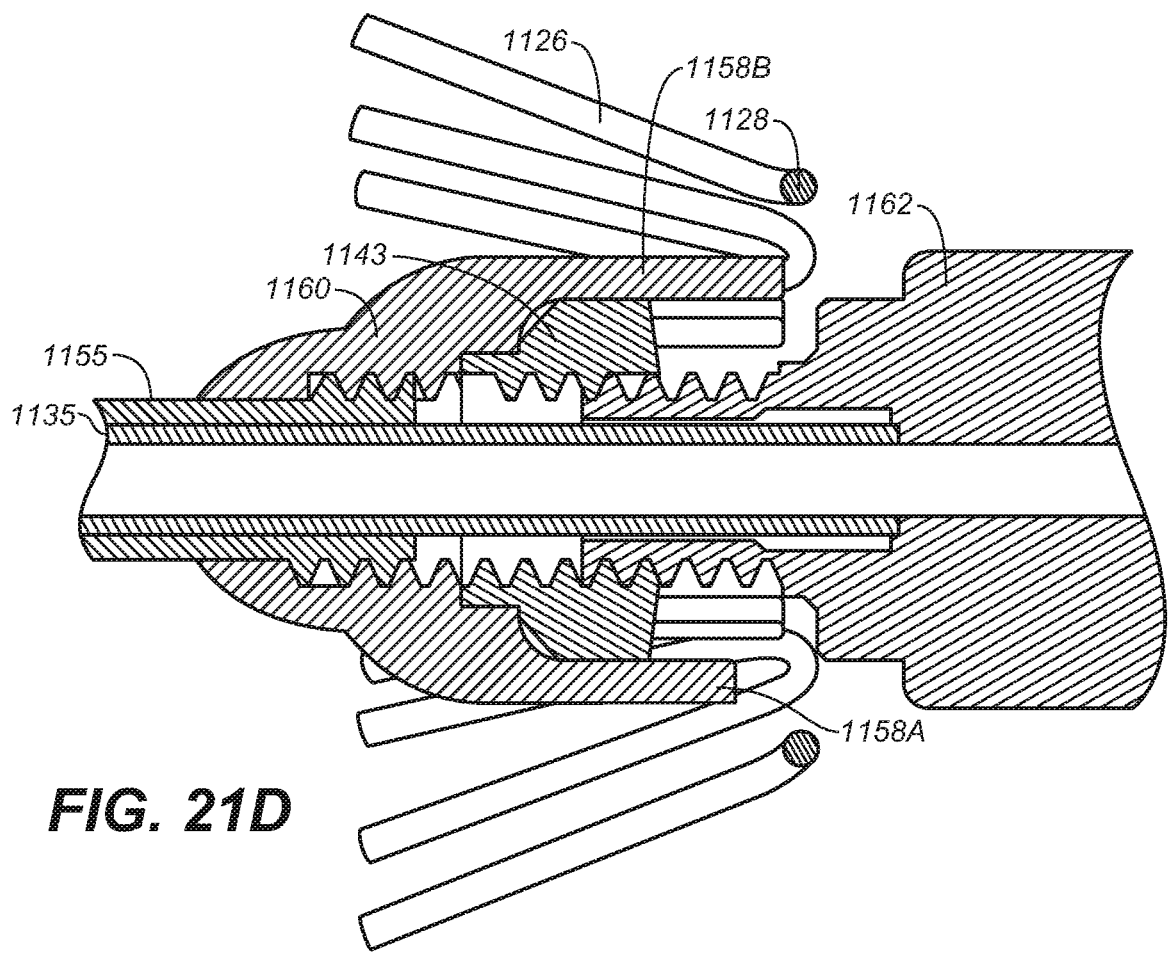

As the nosecone 1162 continues to be turned with respect to the spindle fitting 1143, as shown in FIG. 21D, deployment gaps are opened between the nosecone 1162 and the remaining stent capture fitting arms 1158 including stent capture fitting arm 1158B of the stent capture fitting 1160 permitting the respective crowns 1128 of the bare stent 1126 to pivot outward to complete deployment as seen in FIG. 21D.

The crowns 1128 of the bare stent 1126 have continued to pivot forward because of the bare stent's internal (spring) forces urging its return to its large diameter unrestrained configuration. While the spindle fitting is now released from the nosecone 1162, it is still captured on the nosecone shaft 1135 and will be safely removed as the delivery system is now released from the partially deployed stent graft, it having now been fully deployed. Having a primary and a secondary deployment procedure usable with one delivery system to release crowns of a partially deployed stent provides a utility not previously known in the art.

The drawings and the forgoing description gave examples of embodiments according to the present invention. Numerous variations, whether explicitly given in the specification or not, such as differences in structure, dimension, and use of material, are possible.

What is claimed is:

1. A stent graft delivery system comprising:
a stent capture fitting, said stent capture fitting comprising:
a first circumferential edge; and
a second circumferential edge;
a spindle comprising spindle pins comprising:
a first spindle pin; and
a second spindle pin, wherein prior to motion of said stent capture fitting relative to said spindle pins, a first distance between said first spindle pin and said first circumferential edge is less than a second distance between said second spindle pin and said second circumferential edge.

2. The stent graft delivery system of claim 1 wherein said stent capture fitting comprises stent capture fitting arms.

3. The stent graft delivery system of claim 2 wherein said stent capture fitting arms comprise a first stent capture fitting arm having a length greater than a second stent capture fitting arm of said stent capture fitting arms.

4. The stent graft delivery system of claim 3 wherein said first circumferential edge is at a distal end of said first stent capture fitting arm and said second circumferential edge is at a distal end of said second stent capture fitting arm.

5. A method of deploying a stent graft comprising a proximal anchor stent ring, said method comprising:
restraining proximal apexes of said proximal anchor stent ring between a spindle body of a spindle and a stent capture fitting;
releasing a first proximal apex of said proximal apexes by moving a first circumferential edge of said stent capture fitting past said first proximal apex while a second proximal apex of said proximal apexes remains restrained by said stent capture fitting; and
releasing said second proximal apex by moving a second circumferential edge of said stent capture fitting past said second proximal apex.

6. The method of claim 5 wherein said moving a first circumferential edge of said stent capture fitting and said moving a second circumferential edge of said stent capture fitting comprises retracting said stent capture fitting.

7. The method of claim 5 wherein said capture fitting comprises stent capture fitting arms.

8. The method of claim 7 wherein said stent capture fitting arms comprise a first stent capture fitting arm having a length greater than a second stent capture fitting arm of said stent capture fitting arms.

9. The method of claim 8 wherein said first circumferential edge is at a distal end of said first stent capture fitting arm and said second circumferential edge is at a distal end of said second stent capture fitting arm.

10. A stent graft delivery system comprising:
a spindle shaft;
a spindle coupled to a distal portion of the spindle shaft, the spindle including at least a first spindle pin and a second spindle pin;
a stent capture shaft slidingly disposed over the spindle shaft;
a stent capture fitting coupled to a distal portion of the stent capture shaft, the stent capture fitting including at least a first stent capture fitting arm and a second stent capture fitting arm, a stent capture groove defined between adjacent stent capture fitting arms, wherein the first stent capture fitting arm has a length greater than the second stent capture fitting arm, and
wherein the stent capture fitting is configured to radially restrain proximal apices of a stent graft and movement of the stent capture fitting relative to the spindle sequentially releases the proximal apices.

11. The stent graft delivery system of claim 10, wherein a first circumferential edge is defined at a distal end of the first stent capture fitting arm and a second circumferential edge is defined at a distal end of the second stent capture fitting arm.

12. The stent graft delivery system of claim 11, wherein prior to movement of the stent capture fitting relative to the spindle, a first distance between the first spindle pin and the first circumferential edge is less than a second distance between the second spindle pin and the second circumferential edge.

13. The stent graft delivery system of claim 10, wherein the first spindle pin is configured to receive a first proximal apex of a stent graft and the second spindle pin is configured to receive a second proximal apex of the stent graft.

14. The stent graft delivery system of claim 10, wherein proximal retraction of the stent capture fitting relative to the spindle achieves sequential release of the proximal apices.

15. The stent graft delivery system of claim 10, wherein the stent capture fitting arms are substantially parallel to a central longitudinal axis of the stent capture shaft.

16. The stent graft delivery system of claim 10, wherein the stent capture fitting is fastened to the stent capture shaft.

17. The stent graft delivery system of claim 10, wherein the stent capture fitting is molded directly to the stent capture shaft.

18. The stent graft delivery system of claim 10, further comprising:
    a nosecone shaft; and
    a nosecone coupled to a distal portion of the nosecone shaft, wherein the nosecone shaft is slidingly disposed within the spindle shaft.

19. The stent graft delivery system of claim 10, further comprising:
    a graft cover slidingly disposed over the stent capture shaft, wherein the graft cover is configured to hold the stent graft in a compressed delivery diameter until deployed.

20. The stent graft delivery system of claim 10, wherein following a first stage of deployment that includes proximal retraction of the stent capture fitting relative to the spindle, the first stent capture fitting arm is disposed over the first spindle pin such that a first proximal apex of the stent graft is restrained by the first stent capture fitting arm and the second stent capture fitting arm is disposed proximal to the second spindle pin such that a second proximal apex of the stent graft released.

* * * * *